United States Patent
Al-Shafei et al.

(10) Patent No.: US 12,264,130 B2
(45) Date of Patent: Apr. 1, 2025

(54) PROCESSES FOR AROMATIZATION OF NAPHTHA ISOPARAFFINS

(71) Applicant: Saudi Arabian Oil Company, Dhahran (SA)

(72) Inventors: Emad Naji Al-Shafei, Dhahran (SA); Lianhui Ding, Dhahran (SA); Guanghui Zhu, Dhahran (SA); Mohammed Z. Albahar, Dhahran (SA); Mohammad F. Aljishi, Dhahran (SA); Mohammed A. Alkhunaizi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 154 days.

(21) Appl. No.: 18/324,257

(22) Filed: May 26, 2023

(65) Prior Publication Data

US 2024/0391853 A1    Nov. 28, 2024

(51) Int. Cl.
*C07C 5/41* (2006.01)
*B01D 3/14* (2006.01)
(Continued)

(52) U.S. Cl.
CPC .............. *C07C 5/412* (2013.01); *B01D 3/143* (2013.01); *B01D 15/00* (2013.01); *B01D 19/00* (2013.01);
(Continued)

(58) Field of Classification Search
CPC ........... C07C 5/412; C07C 4/04; C07C 5/393; C07C 5/41; C07C 2529/40; B01D 3/143;
(Continued)

(56) References Cited

U.S. PATENT DOCUMENTS 6,177,601 B1   1/2001  Bogdan et al.
8,722,950 B2   5/2014  van Hal et al.
(Continued)

FOREIGN PATENT DOCUMENTS

JP    2018080130 A1    5/2018

OTHER PUBLICATIONS

Akhtar et al., "Review on the Catalytic Conversion of Naphtha to Aromatics: Advances and Outlook", Energy Fuels 2023, 37, 2586-2607. (Year: 2023).*

*Primary Examiner* — Ali Z Fadhel
(74) *Attorney, Agent, or Firm* — DINSMORE & SHOHL LLP

(57) ABSTRACT

A method for upgrading a naphtha feed includes passing the naphtha feed to an adsorption unit to produce at least a paraffin stream and an isoparaffin stream, wherein the isoparaffin stream comprises isoparaffins and aromatics. Passing the isoparaffin stream to an isoparaffin aromatization catalytic unit that contacts the isoparaffin stream with at least one aromatization catalyst produces aromatics from the isoparaffins thereby yielding an aromatization effluent. The at least one aromatization catalyst may comprise ZSM-5 zeolite. Benzene, toluene, and/or xylene (BTX) may be separated from the aromatization effluent by separating the aromatics effluent into a gas stream and a liquid stream in a gas/liquid separator, wherein the liquid stream contains BTX. Passing the liquid stream to a BTX-separation unit may produce a BTX stream and a recycle stream, wherein the BTX stream contains benzene, toluene, and/or xylene.

17 Claims, 8 Drawing Sheets

(51) Int. Cl.
  *B01D 15/00* (2006.01)
  *B01D 19/00* (2006.01)
  *B01J 29/40* (2006.01)
  *B01J 35/40* (2024.01)
  *C07C 4/04* (2006.01)
  *C07C 5/393* (2006.01)

(52) U.S. Cl.
  CPC ............... *B01J 29/40* (2013.01); *B01J 35/40* (2024.01); *C07C 4/04* (2013.01); *C07C 5/393* (2013.01); *C07C 5/41* (2013.01); *C07C 2529/40* (2013.01)

(58) Field of Classification Search
  CPC .......... B01D 15/00; B01D 19/00; B01J 29/40; B01J 35/40
  See application file for complete search history.

(56) References Cited

U.S. PATENT DOCUMENTS

| | | | |
|---|---|---|---|
| 2008/0255398 A1 | 10/2008 | Stevenson et al. | |
| 2012/0029257 A1* | 2/2012 | Chen .................. | C07C 5/373 585/419 |

* cited by examiner

PROCESSES FOR AROMATIZATION OF NAPHTHA ISOPARAFFINS

BACKGROUND

Field

The present disclosure generally relates to processes for upgrading hydrocarbons and, more specifically, to upgrading naphtha via an aromatization process using ZSM-5 zeolite to benzene, toluene, and xylenes (BTX).

Technical Background

Hydrocarbon feeds, such as naphtha, can be converted to chemical products and intermediates such as olefins and aromatic compounds, which are basic intermediates for a large portion of the petrochemical industry. The worldwide increasing demand for light olefins and aromatic compounds remains a major challenge for many integrated refineries. In particular, the production of some valuable light olefins, such as ethylene, has attracted increased attention as pure olefin streams are considered the building blocks for polymer synthesis. Additionally, aromatic compounds such as benzene, toluene, and xylenes can be valuable intermediates for synthesizing polymers and other organic compounds as well as for fuel additives.

SUMMARY

Accordingly, there is an ongoing need for systems and methods of upgrading hydrocarbons, such as naphtha, to improve yields of desired products, such as aromatics and light olefins. As mentioned hereinabove, aromatic compounds such as benzene, toluene, and xylenes can be valuable intermediates for synthesizing polymers and other organic compounds as well as for fuel additives. Refining processes that utilize naphtha to create light olefins via steam cracking may utilize an adsorption unit to isolate isoparaffins from the naphtha feed before steam cracking to increase ethylene yield. Utilizing the isoparaffins separated from the naphtha feed as a petrochemical feedstock to produce aromatics may be one method by which to increase the yield of aromatics. Further, the processing of naphtha streams, such as light naphtha, may be desirable, as light naphtha possess a low octane number and its use in gasoline production is limited.

According to one or more aspects of the present disclosure, a method for upgrading a naphtha feed can comprise passing the naphtha feed to an adsorption unit to produce at least a paraffin stream and an isoparaffin stream, wherein the isoparaffin stream may comprise isoparaffins and aromatics. The method further comprises passing the isoparaffin stream to an isoparaffin aromatization catalytic unit that contacts the isoparaffin stream with at least one aromatization catalyst to produce aromatics from the isoparaffins thereby yielding an aromatization effluent. The at least one aromatization catalyst may comprise ZSM-5 zeolite.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1A:
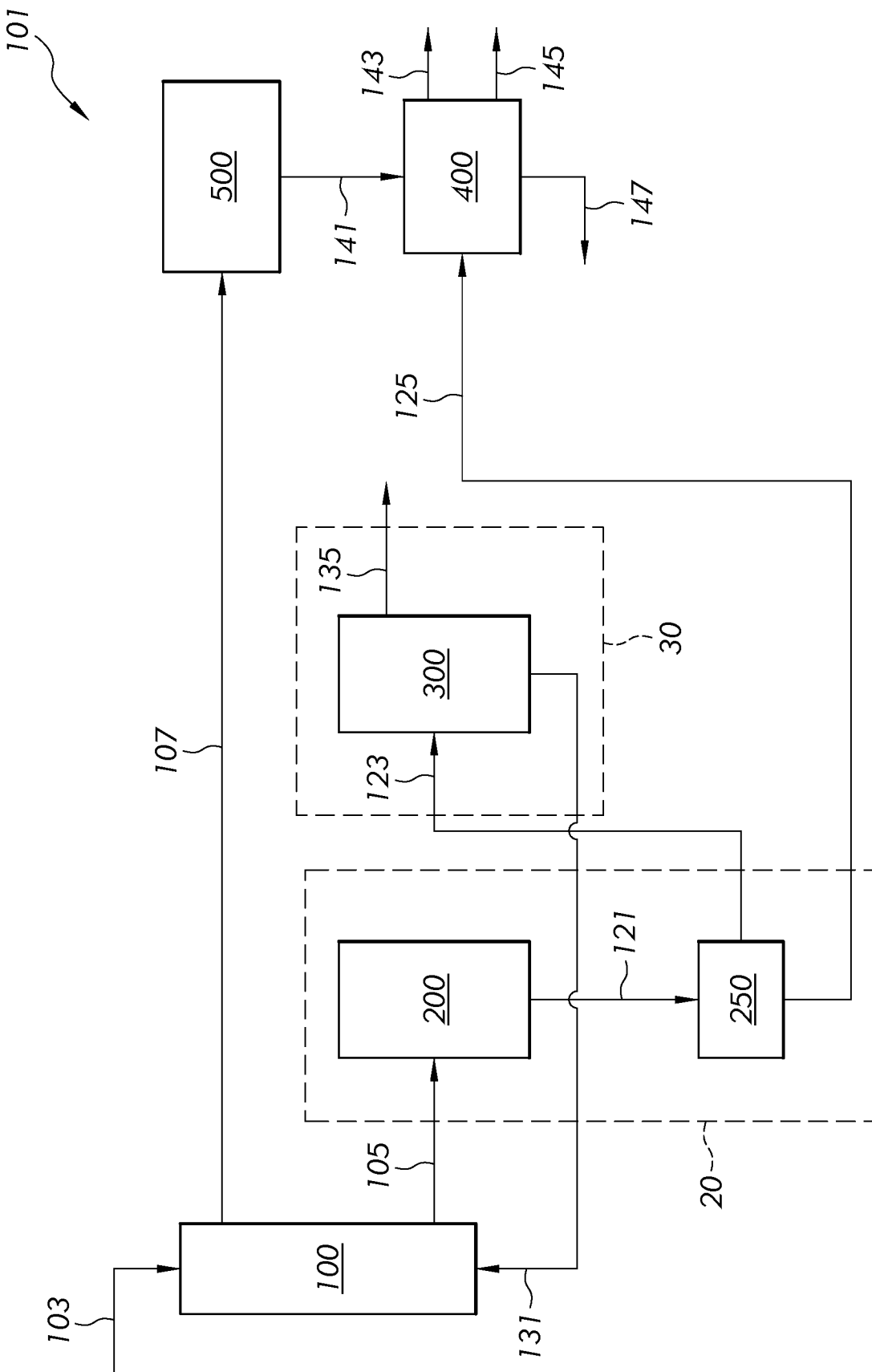
FIG. 1A schematically depicts a generalized flow diagram of a system for upgrading a naphtha feed, according to one or more embodiments shown and described in this disclosure.

For the purpose of describing the simplified schematic illustrations and descriptions of FIGS. 1A, 1B, 1C, 2, and 3 the numerous valves, temperature sensors, electronic controllers, and the like that may be employed and well known to those of ordinary skill in the art of certain chemical processing operations are not included. Further, accompanying components that are often included in chemical processing operations, such as, for example, air supplies, heat exchangers, surge tanks, catalyst hoppers, or other related systems are not depicted. It would be known that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1A, 1B, 1C, 2, and 3. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

The present disclosure is directed a method for upgrading a naphtha feed, the method comprising passing the naphtha feed to an adsorption unit to produce at least a paraffin stream and an isoparaffin stream, wherein the isoparaffin stream comprises isoparaffins and aromatics; and passing the isoparaffin stream to an isoparaffin aromatization catalytic unit that contacts the isoparaffin stream with at least one aromatization catalyst to produce aromatics from the isoparaffins thereby yielding an aromatization effluent, wherein the at least one aromatization catalyst comprises ZSM-5 zeolite.

The various processes and systems of the present disclosure for upgrading naphtha may provide increased efficiency for the upgrading of naphtha compared to conventional processes and systems of upgrading naphtha. That is, the various aromatization processes and systems for upgrading naphtha may increase the conversion of a naphtha feed and may increase the yield of greater value products and intermediates, such as light olefins and gasoline blending components, among other features.

As used in the present disclosure, the term "naphtha" refers to an intermediate mixture of hydrocarbon-containing materials derived from crude oil refining and having atmospheric boiling points from 36 degrees Celsius (° C.) to 220° C. Naphtha may comprise light naphtha comprising hydrocarbon-containing materials having atmospheric boiling points from 36° C. to 80° C., intermediate naphtha comprising hydrocarbon-containing materials having atmospheric boiling points from 80° C. to 140° C., and heavy naphtha comprising hydrocarbon-containing materials having atmospheric boiling points from 140° C. to 200° C. Naphtha may comprise paraffinic, naphthenic, and aromatic hydrocarbons having from 4 carbon atoms to 11 carbon atoms.

As used in the present disclosure, the term "light naphtha" refers to an intermediate mixture of hydrocarbon-containing materials derived from crude oil refining having atmospheric boiling points between 30° C. and 90° C. and consisting of molecules with 5-6 carbon atoms. The isoparaffin content of light naphtha may be from 30 wt. % to 60 wt. %. The paraffin content of light naphtha may be from about 30 wt. %. to about 60 wt. %.

As used in the present disclosure, the term "whole naphtha" refers to an intermediate mixture of hydrocarbon-containing materials derived from crude oil refining having atmospheric boiling points between 90° C. and 157° C. and may comprise aromatics. The whole naphtha may consist of molecules with 4-8 carbon atoms. The isoparaffin content of whole naphtha may be from about 20 wt. % to about 40 wt. %. The paraffin content of whole naphtha may be from about 20 wt. % to about 40 wt. %. The aromatics content of whole naphtha may be from about 10 wt. % to about 50 wt. %.

As used in the present disclosure, the term "straight run naphtha" refers to a mixture of hydrocarbon-containing materials derived from crude oil refining having atmospheric boiling points between 35° C. and 220° C. and may comprise napthenes and aromatics. The straight run naphtha may consist of molecules with 4-11 carbon atoms. The isoparaffin content of whole naphtha may be from about 20 wt. % to about 40 wt. %. The paraffin content of whole naphtha may be from about 20 wt. % to about 40 wt. %. The aromatics content of whole naphtha may be from about 10 wt. % to about 50 wt. %. The napthenes content of whole naphtha may be from about 20 wt. % to about 40 wt. %.

As used in this disclosure, a "catalyst" may refer to any substance that increases the rate of a specific chemical reaction. Catalysts and catalyst components described in this disclosure may be utilized to promote various reactions, such as, but not limited to cracking, aromatic cracking, or combinations of these.

As used in the present disclosure, the term "regenerated catalyst" refers to catalyst that has been contacted with reactants at reaction conditions and then regenerated in a regenerator to heat the catalyst to a greater temperature, oxidize and remove at least a portion of the coke from the catalyst to restore at least a portion of the catalytic activity of the catalyst, or both. The "regenerated catalyst" may have less coke, a greater temperature, or both, compared to used catalyst and may have greater catalytic activity compared to used catalyst. The "regenerated catalyst" may have more coke and lesser catalytic activity compared to fresh catalyst that has not passed through a cracking reaction zone and regenerator.

As used in the present disclosure, the term "deactivated catalyst" refers to a catalyst that has lost function and differs from used catalyst, in that the deactivated catalyst is generally not capable of being regenerated in the regenerator during steady state operation of the regeneration system. The deactivated catalyst can be deactivated by contaminants and/or metals in the hydrocarbon feed or a steam feed depositing on the surfaces of the catalyst.

As used in this disclosure, "cracking" may refer to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. Some catalysts may have multiple forms of catalytic activity, and calling a catalyst by one particular function does not render that catalyst incapable of being catalytically active for other functionality.

As used throughout the present disclosure, the term "light olefins" may refer to one or more of ethylene, propylene, butenes, or combinations of these.

As used throughout the present disclosure, the term "butene" or "butenes" may refer to one or more than one isomer of butene, such as one or more of 1-butene, trans-2-butene, cis-2-butene, isobutene, or mixtures of these isomers. As used throughout the present disclosure, the term "normal butenes" may refer to one or more than one of 1-butene, trans-2-butene, cis-2-butene, or mixtures of these isomers, and does not include isobutene. As used throughout the present disclosure, the term "2-butene" may refer to trans-2-butene, cis-2-butene, or a mixture of these two isomers.

As used throughout the present disclosure, the terms "upstream" and "downstream" may refer to the relative positioning of unit operations with respect to the direction of flow of the process streams. A first unit operation of a system may be considered "upstream" of a second unit operation if process streams flowing through the system encounter the first unit operation before encountering the second unit operation. Likewise, a second unit operation may be considered "downstream" of the first unit operation if the process streams flowing through the system encounter the first unit operation before encountering the second unit operation.

As used in the present disclosure, passing a stream or effluent from one unit "directly" to another unit may refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined. Simply dividing a stream into two streams having the same composition is also not considered to comprise an intervening system that changes the composition of the stream.

As used in this disclosure, a "reactor" refers to any vessel, container, or the like, in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed-bed reactors, and fluidized bed reactors. One or more "reaction zones" may be disposed within a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided or separated into two or more process streams of desired composition. It should be additionally understood that where only one separation unit is depicted in a figure or described, two or more separation units may be employed to carry out the identical or substantially identical separation. For example, where a distillation column with multiple outlets is described, it is contemplated that several separators arranged in series may equally separate the feed stream and such embodiments are within the scope of the presently described embodiments.

As used in this disclosure, the term "effluent" may refer to a stream that is passed out of a reactor, a reaction zone, or a separation unit following a particular reaction or separation. Generally, an effluent has a different composition than the stream that entered the separation unit, reactor, or reaction zone. It should be understood that when an effluent is passed to another system unit, only a portion of that system stream may be passed. For example, a slip stream (having the same composition) may carry some of the effluent away, meaning that only a portion of the effluent may enter the downstream system unit. The term "reaction effluent" may more particularly be used to refer to a stream that is passed out of a reactor or reaction zone.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrogen stream" passing to a first system component or from a first system component to a second system component should be understood to equivalently disclose "hydrogen" passing to the first system component or passing from a first system component to a second system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in one or more embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in some embodiments, less than all of the streams signified by an arrow may be transported between the system components, such as if a slip stream is present.

According to one or more embodiments, a naphtha feed may be upgraded by a series of processing steps. As described herein, the naphtha feed is passed to an adsorption unit to produce at least a paraffins stream and an isoparaffins stream. The isoparaffins stream comprises isoparaffins and aromatics. The isoparaffins stream is passed to an isoparaffin aromatization catalytic unit. Then, a third reaction may reduce the oxidized metal by use of the carbon monoxide from the first reaction. These embodiments, as well as others, are described hereinbelow in detail Configuration I Now referring to FIG. 1A, a system 101 for upgrading a naphtha feed 103, containing at least light naphtha, includes an adsorption unit 100 and an isoparaffin aromatization catalytic unit 200 downstream of the adsorption unit 100, and may further include a steam cracking unit 500 downstream of the adsorption unit 100. The adsorption unit 100 is operable to contact the naphtha feed 103 into at least an isoparaffins stream 105 and a paraffins stream 107. The isoparaffin aromatization catalytic unit 200 is operable to contact the isoparaffins stream 105 in the presence of at least one aromatization catalyst. Contacting the isoparaffins stream 105 in the presence of at least one aromatization catalyst produces an aromatization effluent 121 having a greater concentration of aromatics compared to the isoparaffins stream 105.

The system 101 may further include a gas/liquid separation unit 250 downstream of the isoparaffin aromatization catalytic unit 200, a BTX separation unit 300 downstream of the gas/liquid separation unit 250, and a gas separation unit 400 downstream of the gas/liquid separation unit 250. The gas/liquid separation unit 250 may be operable to separate the aromatization effluent 121 into a liquid stream 123 and a gas stream 125. The BTX separation unit may be operable to contact the liquid stream 123 into at least an aromatics effluent 135 and an unconverted aromatics stream 131. The aromatics effluent 135 may comprise at least benzene, toluene, xylenes, and/or a combination of these. The unconverted aromatics stream 131 may comprise at least unconverted isoparaffins.

The steam cracking unit 500 may be operable to contact the paraffins stream 107 into at least an ethylene stream 141. The gas separation unit 400 is also downstream of the of the steam cracking unit 500. The gas separation unit 400 is operable to contact the ethylene stream 141 and gas stream 125 into at least an olefins stream 143, a byproduct stream 145, and an aromatic-rich stream 147.

Adsorption Unit

It will be appreciated by those skilled in the art that the boiling point may range between various operations and between various sources of the naphtha feed 103. The naphtha feed 103 may be a naphtha from any source. In embodiments, the naphtha of the naphtha feed 103 may comprise light naphtha.

In embodiments, the isoparaffin content of the naphtha feed 103 in the system 101 may be greater than or equal to 30 wt. % and less than or equal to 60 wt. % isoparaffin content. In embodiments, the isoparaffin content of the naphtha feed 103 may be greater than or equal to 30 wt. %, greater than or equal to 35 wt. %, greater than or equal to 40 wt. %, or even greater than or equal 45 wt. %. In embodiments, the isoparaffin content of the naphtha feed 103 may be less than or equal to 60 wt. %, less than or equal to 55 wt. %, or even less than or equal to 50 wt. %. In embodiments, the isoparaffin content of the naphtha feed 103 may be greater than or equal to 30 wt. % and less than or equal to 35 wt. %, greater than or equal to 35 w. % and less than or equal to 40 wt. %, greater than or equal to 40 wt. % and less than or equal to 45 wt. %, greater than or equal to 45 wt. % and less than or equal to 50 wt. %, greater than or equal to 50 wt. % and less than or equal to 55 wt. %, or even greater than or equal to 55 wt. % and less than or equal to 60 wt. %, or any and all sub-ranges formed from any of these endpoints.

In embodiments, the paraffin content of the naphtha feed 103 in the system 101 may be greater than or equal to 30 wt. % and less than or equal to 60 wt. %. In embodiments, the paraffin content of the naphtha feed 103 may be greater than or equal to 30 wt. %, greater than or equal to 35 wt. %, greater than or equal to 40 wt. %, or even greater than or equal 45 wt. %. In embodiments, the paraffin content of the naphtha feed 103 may be less than or equal to 60 wt. %, less than or equal to 55 wt. %, or even less than or equal to 50 wt. %. In embodiments, the paraffin content of the naphtha feed 103 may be greater than or equal to 30 wt. % and less than or equal to 35 wt. %, greater than or equal to 35 w. % and less than or equal to 40 wt. %, greater than or equal to 40 wt. % and less than or equal to 45 wt. %, greater than or equal to 45 wt. % and less than or equal to 50 wt. %, greater than or equal to 50 wt. % and less than or equal to 55 wt. %, or even greater than or equal to 55 wt. % and less than or equal to 60 wt. %, or any and all sub-ranges formed from any of these endpoints.

The naphtha feed 103 may comprise a nominal boiling temperature range greater than or equal to 36° C. and less than or equal to 80° C. In embodiments, the boiling temperature range of the naphtha feed 103 may be greater than or equal to 36° C., greater than or equal to 45° C., or even greater than or equal to 60° C. In embodiments, the boiling temperature range of the naphtha feed 103 may be less than or equal to 80° C., or even less than or equal to 70° C. In embodiments, the boiling temperature range of the naphtha feed 103 may be greater than or equal to 36° C. and less than or equal to 45° C., greater than or equal to 45° C. and less than or equal to 60° C., greater than or equal to 60° C. and less than or equal to 70° C., or even greater than or equal to 70° C. and less than or equal to 80° C., or any and all sub-ranges formed from any of these endpoints.

The naphtha feed 103 may comprise greater than 0.1 parts per million by weight (ppmw) and less than 2000 ppmw of sulfur components. In embodiments, the naphtha feed 103 may comprise sulfur components greater than or equal to 0.1 ppmw, greater than or equal to 0.5 ppmw, greater than or equal to 1 ppmw, greater than or equal to 3 ppmw, or even greater than or equal to 5 ppmw. In embodiments, the naphtha feed 103 may comprise sulfur components less than or equal to 2000 ppmw or even less than or equal to 1000 ppmw. In embodiments, the naphtha feed 103 may comprise sulfur components greater than or equal to 0.1 ppmw and less than or equal to 0.5 ppmw, greater than or equal to 0.5 ppmw and less than or equal to 1 ppmw, greater than or equal to 1 ppmw and less than or equal to 3 ppmw, greater than or equal to 3 ppmw and less than or equal to 1000 ppmw, greater than or equal to 1000 ppmw and less than or equal to 2000 ppmw, or any and all sub-ranges formed from any of these endpoints.

The naphtha feed 103 may be passed directly to the adsorption unit 100 without passing through any intervening reactor or separation system. The unconverted aromatics stream 131 may also be passed to the adsorption unit 100 from the BTX separation unit 300 without passing through any intervening reactor or separation system. The adsorption unit 100 may be in fluid communication with the BTX separation unit 300.

The adsorption unit 100 may be operable to separate the naphtha feed 103 and/or the unconverted aromatics stream 131 into at least a paraffins stream 107 and an isoparaffins stream 105. The adsorption unit 100 may include any type of reactor suitable for contacting the naphtha feed 103. The adsorption unit 100 may be conducted in 3-phase steps and may include hydrogen ($H_2$), light hydrocarbons, high octane product, and solid catalyst.

The adsorption unit 100 may operate at a temperature greater than or equal to 100° C. and less than or equal to 280° C. In embodiments, the temperature of the adsorption unit 100 may be greater than or equal to 100° C., greater than or equal to 110° C., or even greater than or equal to 120° C. In embodiments, the temperature of the adsorption unit 100 may be less than or equal to 280° C. or even less than or equal to 250° C. In embodiments, the temperature of the adsorption unit 100 may be greater than or equal to 100° C. and less than or equal to 110° C. greater than or equal to 110° C. and less than or equal to 120° C., greater than or equal to 120° C. and less than or equal to 250° C., greater than or equal to 250° C. and less than or equal to 280° C., or any and all sub-ranges formed from any of these endpoints.

The adsorption unit 100 may operate at a pressure greater than or equal to 1 MPa (10 bar) and less than or equal to 5 MPa (50 bar). In embodiments, the adsorption unit 100 may operate at a pressure of greater than or equal to 1 MPa, greater than or equal to 1.5 MPa, or even greater than or equal to 2 MPa. In embodiments, the adsorption unit 100 may operate at a pressure of less than or equal to 5 MPa, less than or equal to 4.5 MPa, or even less than or equal to 4 MPa. In embodiments, the adsorption unit 100 may operate at a pressure of greater than or equal to 1 MPa and less than or equal to 1.5 MPa, greater than or equal to 1.5 MPa and less than or equal to 2 MPa, greater than or equal to 2 MPa and less than or equal to 4 MPa, greater than or equal to 4 MPa and less than or equal to 4.5 MPa, greater than or equal to 4.5 MPa and less than or equal to 5 MPa, or any and all sub-ranges formed from any of these endpoints.

The absorbent positioned within the adsorption unit 100 may be a molecular sieve or silica gel combined with a molecular sieve. The molecular sieve may comprise zeolites. Zeolites are ordered, porous crystalline materials having a definite crystalline structure. Within their crystalline structure, zeolites have cavities interconnected by channels or pores, which accept for adsorption molecules of certain dimensions while rejecting those of dimensions that are too large to be adsorbed through the channels and pores.

The isoparaffins stream 105 may be greater than or equal to 10 wt. % and less than or equal to 90 wt. % isoparaffins. In embodiments, the isoparaffins stream 105 may be greater than or equal to 30 wt. % and less than or equal to 60 wt. % isoparaffins. In embodiments, the isoparaffins content of the isoparaffins stream 105 may be greater than or equal to 10 wt. %, greater than or equal to 20 wt. %, or even greater than or equal to 30 wt. %. In embodiments, the isoparaffins content of the isoparaffins stream 105 may be less than or equal to 90 wt. %, less than or equal to 80 wt. %, or even less than or equal to 70 wt. %. In embodiments, the isoparaffins content of the isoparaffins stream 105 may be greater than or equal to 10 wt. % and less than or equal to 20 wt. %, greater than or equal to 20 wt. % and less than or equal to 30 wt. %, greater than or equal to 30 wt. % and less than or equal to 40 wt. %, greater than or equal to 40 wt. % and less than or equal to 50 wt. %, greater than or equal to 50 wt. % and less than or equal to 60 wt. %, greater than or equal to 60 wt. % and less than or equal to 70 wt. %, greater than or equal to 70 wt. % and less than or equal to 80 wt. %, greater than or equal to 80 wt. % and less than or equal to 90 wt. %, or any and all sub-ranges formed from any of these endpoints.

The paraffins stream 107 may be greater than or equal to 10 wt. % and less than or equal to 70 wt. % paraffins. In embodiments, the paraffins stream 107 may be greater than or equal to 30 wt. % and less than or equal to 60 wt. % isoparaffins. In embodiments, the isoparaffins content of the paraffins stream 107 may be greater than or equal to 10 wt. %, greater than or equal to 20 wt. %, or even greater than or equal to 30 wt. %. In embodiments, the isoparaffins content of the paraffins stream 107 may be less than or equal to 70 wt. %, less than or equal to 65 wt. %, or even less than or equal to 60 wt. %. In embodiments, the isoparaffins content of the paraffins stream 107 may be greater than or equal to 10 wt. % and less than or equal to 20 wt. %, greater than or equal to 20 wt. % and less than or equal to 30 wt. %, greater than or equal to 30 wt. % and less than or equal to 60 wt. %, greater than or equal to 60 wt. % and less than or equal to 65 wt. %, greater than or equal to 65 wt. % and less than or equal to 70 wt. %, or even greater than or equal to 30 wt. % and less than or equal to 60 wt. %, or any and all sub-ranges formed from any of these endpoints.

Isoparaffin Aromatization Catalytic Unit

Still referring to FIG. 1A, the system 101 includes the isoparaffin aromatization catalytic unit 200, which may be disposed downstream of the adsorption unit 100. The isoparaffin aromatization catalytic unit 200 may be part of an aromatization system 20 that includes a gas/liquid separation unit 250 in addition to the isoparaffin aromatization catalytic unit 200. The isoparaffin aromatization catalytic unit 200 may be in fluid communication with the adsorption unit 100 and may receive all or a portion of the isoparaffins stream 105 from the adsorption unit 100.

In one embodiment, the isoparaffins stream 105 may be passed directly from the adsorption unit 100 to the isoparaffin aromatization catalytic unit 200 without passing through any intervening reactor or separation system. The isoparaffin aromatization catalytic unit 200 may be operable to contact at least a portion of the isoparaffins stream 105 in the presence of at least one aromatization catalyst to produce an aromatization effluent 121. The isoparaffin aromatization catalytic unit 200 may include any type of reactor suitable for contacting the isoparaffins stream 105 in the presence of the at least one aromatization catalyst. Suitable reactors may include, but are not limited to, fixed-bed reactors, moving bed reactors, fluidized bed reactors, plug flow reactors, other type of reactor, or combinations of reactors. The isoparaffin aromatization catalytic unit 200 may include one or more fixed-bed reactors, which may be operated in downflow, upflow, or horizontal flow configurations.

The isoparaffin aromatization catalytic unit 200 may be any one of several types of catalytic reforming process configurations, which differ in the manner in which they regenerate the reforming catalyst to remove the coke formed during the reforming process. Catalyst regeneration, which involves combusting detrimental coke in the presence of oxygen, can include a semi-regenerative process, a cyclic regeneration process, or continuous regeneration process. Semi-regeneration is the simplest configuration, and the entire unit, including all reactors in the series, are shut-down for catalyst regeneration in all reactors. Cyclic configurations utilize an additional "swing" reactor to permit one reactor at a time to be taken off-line for regeneration while the others remain in service. Continuous catalyst regeneration configurations, which are the most complex, provide for continuous operation by catalyst removal, regeneration and replacement. While continuous catalyst regeneration configurations may enable the severity of the operating conditions to be increased due to higher catalyst activity, the associated capital investment is necessarily higher.

Figure 1B:
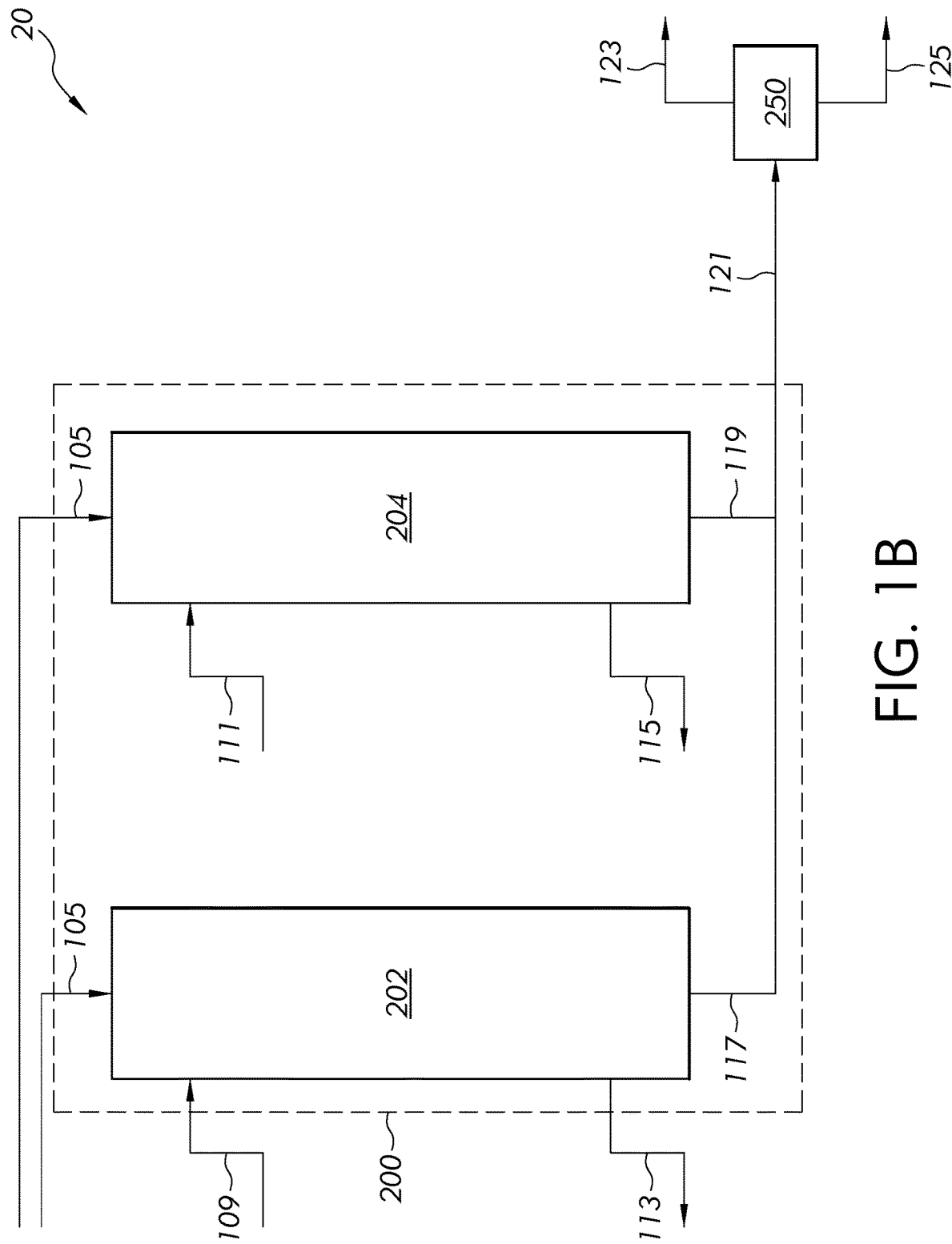
FIG. 1B schematically depicts a generalized flow diagram of an isoparaffin aromatization catalytic unit of the system of FIG. 1A, according to one or more embodiments shown and described in this disclosure.

Now referring to FIG. 1B, two swing reactors, a first aromatization reactor 202 and a second aromatization reactor 204, are depicted in the aromatization system 20. However, it is contemplated that any number of swing reactors may be utilized in other embodiments, such as, but not limited to, three or four swing reactors. The first and second aromatization reactors, 202 and 204, may contact the isoparaffins stream 105 in the presence of the at least one aromatization catalyst at operating conditions sufficient to cause at least a portion of the hydrocarbons in the isoparaffins stream 105 to undergo aromatization to produce a first aromatization effluent 117 and second aromatization effluent 119, where the first and second aromatization effluents, 117 and 119, comprise aromatics. The first and second aromatization effluents 117 and 119 may be become the aromatization effluent 121 to feed into the gas/liquid separation unit 250.

In embodiments, the conversion cycle utilizes the first aromatization reactor 202 for time-on-stream from 8-24 hours. Then the isoparaffins stream 105 may switch to the second aromatization reactor 204 in order to continue the catalytic conversion of isoparaffin to aromatics. After a first cycle is completed, the reactor will switch off the isoparaffins stream 105 and evacuate. Then the first aromatization reactor 202 would increase temperature to between 600° C. or 700° C. and introduce air or an air mixture with a nitrogen stream and that would be introduced to the first aromatization reactor 202 via line 109 and vented via line 113 in order to conduct a de-coking cycle, re-generate the catalysts bed, and prepare the catalysts bed for another conversion cycle.

Similarly, in the second aromatization reactor 204 the air and air mixture with nitrogen would be introduced via line 111 and subsequently vented out via line 115. The gas vented of both aromatization reactors, 202 and 204, are analyzed via on-line gas analyzer to measure carbon dioxide ($CO_2$) concentration. Once the $CO_2$ concentration is reduced to 0.2 wt %, the de-coking step stop and nitrogen gas will be introduced for 15-60 minutes, in order to make the catalytic reactor ready for next isoparaffin conversion cycle.

The first and second aromatization reactors, 202 and 204, may operate such that while the first aromatization reactor 202 is converting isoparaffins to aromatics, the second aromatization reactor 204 may regenerate the catalyst. Similarly, while the s aromatization reactor 202 is undergoing the catalyst regeneration procedure, the second aromatization reactor 204 may convert isoparaffins to aromatics. A similar mode of operation may continue for the use of more than two reactors.

The at least one aromatization catalyst comprises ZSM-5. As used in the present disclosure, "ZSM-5" refers to zeolites having an MFI framework type according to the IUPAC zeolite nomenclature and consisting of silica and alumina.

ZSM-5 refers to "Zeolite Socony Mobil-5" and is a pentasil family zeolite that can be represented by the chemical formula $Na_nAl_nSi_{96-n}O_{192} \cdot 16H_2O$, where 0<n<27. In embodiments, the molar ratio of silica to alumina in the ZSM-5 may be greater than or equal to 20 and less than or equal to 200. When the silica to alumina ratio is too low (i.e., less than 20), the catalyst may be too acidic and have a strong tendency to coke. When the silica to alumina ratio is too high (i.e., more than 250), the catalyst may have a weak acidity and be less reactive.

In embodiments, the molar ratio of silica to alumina in the ZSM-5 may be greater than or equal to 20, greater than or equal to 50, or even greater than or equal to 100. In embodiments, the molar ratio of silica to alumina in the ZSM-5 may be less than or equal to 250, less than or equal to 200, or even greater than or equal to 150. In embodiments, the molar ratio of silica to alumina in the ZSM-5 may be greater than or equal to 20 and less than or equal to 50, greater than or equal to 50 and less than or equal to 100, greater than or equal to 100 and less than or equal to 150, greater than or equal to 150 and less than or equal to 200, greater than or equal to 200 and less than or equal to 250, or even greater than or equal to 100 and less than or equal to 150, or any and all sub-ranges formed from any of these endpoints.

MFI zeolite of ZSM-5 may be made from sub-micro crystal scale and nano crystal scale greater than or equal to 100 nm and less than or equal to 750 nm. When the MFI zeolite has a larger nano crystal scale (i.e., greater than 750 nm), diffusion will be longer, and the internal channels have a tendency to coke. Shorter nano crystal scales generally promote faster diffusion with less tendency to coke. In embodiments, the micro crystal scale and nano crystal scale may be greater than or equal to 100 nm, greater than or equal to 150 nm, or even greater than or equal to 200 nm. In embodiments, the micro crystal scale and nano crystal scale may be less than or equal to 750 nm or even less than or equal to 700 nm. In embodiments, the micro crystal scale and nano crystal scale may be greater than or equal to 100 nm and less than or equal to 150 nm, greater than or equal to 150 nm and less than or equal to 200 nm, greater than or equal to 200 nm and less than or equal to 700 nm, greater than or equal to 700 nm and less than or equal to 750 nm, or any and all sub-ranges formed from any of these endpoints.

In order to enhance catalytic aromatization reaction of isoparaffins, the MFI zeolite may be modified by combining the MFI ZSM-5 zeolite with a thin layer coating by another MFI of silicalite-1 or boron silicalite-1. The combined MFI zeolite of ZSM-5 may be coated with a thin layer with amorphous silica, alumina, silica and zinc oxide with silica with phosphorus oxide. The modified MFI ZSM-5 catalyst may be coated with alumina binder between 20 wt. % to 60 wt. %, preferably between 30 wt. % to 50 wt. %, to increase crush strength and thermal resistance of the catalyst during the reaction and air re-generation. Importantly, the modified MFI zeolite catalyst does not utilize any noble metals which are sensitive to sulfur content, which may be present in isoparaffin streams.

The first and second aromatization reactors, 202 and 204, may operate at a temperature in the range greater than or equal to 350° C. (662° F.) and less than or equal to 550° C. (1022° F.), and an operating pressure greater than or equal to 0.2 MPa (2 bar) and less than or equal to 2.5 MPa (25 bar). In embodiments, the first and second aromatization reactors, 202 and 204, may operate at a temperature greater than or equal to 400° C. and less than or equal to 475° C. In embodiments, the first and second aromatization reactors, 202 and 204, may operate at a temperature of greater than or equal to 350° C., greater than or equal to 375° C., or even greater than or equal to 400° C. In embodiments, the first and second aromatization reactors, 202 and 204, may operate at a temperature of less than or equal to 550° C., less than or equal to 525° C., less than or equal to 500° C., or even less than or equal to 475° C. In embodiments, the first and second aromatization reactors, 202 and 204, may operate at a temperature of greater than or equal to 350° C. and less than or equal to 375° C., greater than or equal to 375° C. and less than or equal to 400° C. greater than or equal to 400° C. and less than or equal to 500° C., greater than or equal to 500° C. and less than or equal to 525° C., greater than or equal to 525° C. and less than or equal to 550° C., or any and all sub-ranges formed from any of these endpoints. In embodiments, the first and second aromatization reactors, 202 and 204, may operate at a pressure greater than or equal to 0.5 MPa and less than or equal to 1.5 MPa. In embodiments, the first and second aromatization reactors, 202 and 204, may operate at a pressure greater than or equal to 0.2 MPa, greater than or equal to 0.25 MPa, greater than or equal to 0.3 MPa, greater than or equal to 0.35 MPa, or even greater than or equal to 0.4 MPa. In embodiments, the first and second aromatization reactors, 202 and 204, may operate at a pressure less than or equal to 2.5 MPa, less than or equal to 2.0 MPa, or even less than or equal to 1.5 MPa. In embodiments, the first and second aromatization reactors, 202 and 204, may operate at a pressure greater than or equal to 0.2 MPa and less or equal to 0.25 MPa, greater than or equal to 0.25 MPa and less than or equal to 0.3 MPa, greater than or equal to 0.3 MPa and less than or equal to 0.35 MPa, greater than or equal to 035 MPa and less or equal to 0.4 MPa, greater than or equal to 0.4 MPa and less than or equal to 1.5 MPa, greater than or equal to 1.5 MPa and less than or equal to 2.0 MPa, greater than or equal to 2.0 MPa and less or equal to 2.5 MPa, or any and all sub-ranges formed from any of these endpoints.

The first and second aromatization reactors, 202 and 204, may operate at a liquid hourly space velocity (LHSV) greater than or equal to 0.1 $h^{-1}$ and less than or equal to 20 $h^{-1}$. In embodiments, the first and second aromatization reactors, 202 and 204, may operate at an LHSV greater than or equal to 0.5 $h^{-1}$ and less than or equal to 3 $h^{-1}$. In embodiments, the first and second aromatization reactors, 202 and 204, may operate at an LHSV greater than or equal to 0.1 $h^{-1}$, greater than or equal to 0.25 $h^{-1}$, or even greater than or equal to 0.5 $h^{-1}$. In embodiments, the first and second aromatization reactors, 202 and 204, may operate at an LHSV less than or equal to 20 $h^{-1}$, less than or equal to 15 $h^{-1}$, less than or equal to 10 $h^{-1}$, or even less than or equal to 5 $h^{-1}$. In embodiments, the first and second aromatization reactors, 202 and 204, may operate at an LHSV greater than or equal to 0.1 $h^{-1}$ and less than or equal to 0.25 $h^{-1}$, greater than or equal to 0.25 $h^{-1}$ and less than or equal to 0.5 $h^{-1}$, greater than or equal to 0.5 $h^{-1}$ and less than or equal to 10 $h^{-1}$, greater than or equal to 10 $h^{-1}$ and less than or equal to 15 $h^{-1}$, greater than or equal to 15 $h^{-1}$ and less than or equal to 20 $h^{-1}$, or even greater than or equal to 0.5 $h^{-1}$ and less than or equal to 5 $h^{-1}$, or any and all sub-ranges formed from any of these endpoints.

In embodiments, the aromatics content of the aromatization effluent 121 may be greater than or equal to 10 wt. % and less than or equal to 90 wt. %. In embodiments, the aromatics content of the aromatization effluent 121 may be greater than or equal to 20 wt. % and less than or equal to 70 wt. %. In embodiments, the aromatics content of the aromatization effluent 121 may be greater than or equal to 10 wt. %, greater than or equal to 15 wt. %, or even greater than or equal to 20 wt. %. In embodiments, the aromatics content of the aromatization effluent 121 may be less than or equal to 90 wt. %, less than or equal 80 wt. %, or even less than or equal to 70 wt. %. In embodiments, the aromatics content of the aromatization effluent 121 may be greater than or equal to 10 wt. % and less than or equal to 15 wt. %, greater than or equal to 15 wt. % and less than or equal to 20 wt. %, greater than or equal to 20 wt. % and less than or equal to 70 wt. %, greater than or equal to 70 wt. % and less than or equal to 80 wt. %, greater than or equal to 80 wt. % and less than or equal to 90 wt. %, or any and all sub-ranges formed from any of these endpoints.

Referring again to FIG. 1A, contacting the isoparaffins stream 105 in the presence of the at least one aromatization catalyst at the disclosed operating conditions may cause at least a portion of isoparaffinic compounds in the isoparaffins stream 105 to undergo aromatization reactions to form aromatics. The isoparaffin aromatization catalytic unit 200 may be in fluid communication with the gas/liquid separation unit 250 to pass the aromatization effluent 121 from the isoparaffin aromatization catalytic unit 200 to the gas/liquid separation unit 250.

Gas/Liquid Separation Unit

Referring again to FIG. 1A, the system 101 may include the gas/liquid separation unit 250, which may be disposed downstream of the isoparaffin aromatization catalytic unit 200. The gas/liquid separation unit 250 may be in fluid communication with the isoparaffin aromatization catalytic unit 200 and may receive all or a portion of the aromatization effluent 121 from the isoparaffin aromatization catalytic unit 200. The gas/liquid separation unit 250 may include one or a plurality of separation units.

The aromatization effluent 121 may be passed directly from the isoparaffin aromatization catalytic unit 200 to gas/liquid separation unit 250 without passing through any intervening reactor or separation system. The gas/liquid separation unit 250 may be operable to separate the aromatization effluent 121 into at least the gas stream 125 and the liquid stream 123.

The gas/liquid separation unit 250 may operate at a temperature greater than or equal to negative 20° C. (−20° C.) and less than or equal to 15° C. In embodiments, the gas/liquid separation unit 250 may operate at a temperature greater than or equal to −5° C. and less than or equal to 10° C. In embodiments, the gas/liquid separation unit 250 may operate at a temperature greater than or equal to −20° C., greater than or equal to −15° C., greater than or equal to −10° C., or even greater than or equal to −5° C. In embodiments, the gas/liquid separation unit 250 may operate at a temperature less than or equal to 15° C. or even less than or equal to 10° C. In embodiments, the gas/liquid separation unit may operate at a temperature greater than or equal to −20° C. and less than or equal to −15° C., greater than or equal to −15° C. and less than or equal to −10° C., greater than or equal to −10° C. and less than or equal to −5° C., greater than or equal to −5° C. and less than or equal to 10° C., greater than or equal to 10° C. and less than or equal to 15° C., or any and all sub-ranges formed from any of these endpoints.

In embodiments, the aromatics content of the liquid stream 123 may be greater than or equal to 10 wt. % and less than or equal to 90 wt. %. In embodiments, the aromatics content of the liquid stream 123 may be greater than or equal to 20 wt. % and less than or equal to 70 wt. %. In embodiments, the aromatics content of the liquid stream 123 may be greater than or equal to 10 wt. %, greater than or equal to 15 wt. %, or even greater than or equal to 20 wt. %. In embodiments, the aromatics content of the liquid stream 123 may be less than or equal to 90 wt. %, less than or equal to 80 wt. %, or even less than or equal to 70 wt. %. In embodiments, the aromatics content of the liquid stream 123 may be greater than or equal to 10 wt. % and less than or equal to 15 wt. %, greater than or equal to 15 wt. % and less than or equal 20 wt. %, greater than or equal 20 wt. % and less than or equal to 70 wt. %, greater than or equal to 70 wt. % and less than or equal to 80 wt. %, greater than or equal to 80 wt. % and less than or equal 90 wt. %, or any and all sub-ranges formed from any of these endpoints.

In embodiments, the aromatics content of the liquid stream 123 in the system 101 may be greater than or equal to 70 wt. % and less than or equal to 95 wt. %. In embodiments, the aromatics content of the liquid stream 123 may be greater than or equal to 70 wt. %, greater than or equal to 75 wt. %, or even greater than or equal to 80 wt. %. In embodiments, the aromatics content of the liquid stream 123 may be less than or equal to 95 wt. %, less than or equal to 90 wt. %, or even less than or equal to 85 wt. %. In embodiments, the aromatics content of the liquid stream 123 may be greater than or equal to 70 wt. % and less than or equal to 75 wt. %, greater than or equal to 75 wt. % and less than or equal to 80 wt. %, greater than or equal to 80 wt. % and less than 85 wt. %, greater than or equal to 85 wt. % and less than or equal to 90 wt. %, or even greater than or equal to 90 wt. % and less than or equal to 95 wt. %, or any and all sub-ranges formed from any of these endpoints.

In embodiments, the contents of the gas stream 125 in the system 101 may be mostly alkanes separated from the aromatization effluent 121. The alkane composition of the aromatization effluent 121 may be 1-20 wt. % methane, 1-20 wt. % ethane, 10-40 wt. % propane, 10-30 wt. % butane, and 1-5 wt. % pentane.

BTX Separation Unit

Referring again to FIG. 1A, the system 101 may include the BTX separation unit 300, which may be disposed downstream of the gas/liquid separation unit 250. The BTX separation unit 300 may be in fluid communication with the gas/liquid separation unit 250 and may receive all or a portion of the liquid stream 123 from the gas/liquid separation unit 250. The BTX separation unit 300 may include one or a plurality of separation units.

The liquid stream 123 may be passed directly from the gas/liquid separation unit 250 to the BTX separation unit 300 without passing through any intervening reactor or separation system. The BTX separation unit 300 may be operable to separate the liquids stream 123 into at least the aromatics effluent 135 and the unconverted aromatics stream 131. The unconverted aromatics stream 131 may be recycled to the adsorption unit 100. In alternative embodiments, the unconverted aromatics stream 131 may be sent to the gasoline pool. The aromatics effluent 135 may comprise at least benzene, toluene, xylenes, and/or a combination of these. The unconverted aromatics stream 131 may comprise at least some isoparaffins. The BTX separation unit 300 may be in fluid communication with the adsorption unit 100.

Figure 1C:
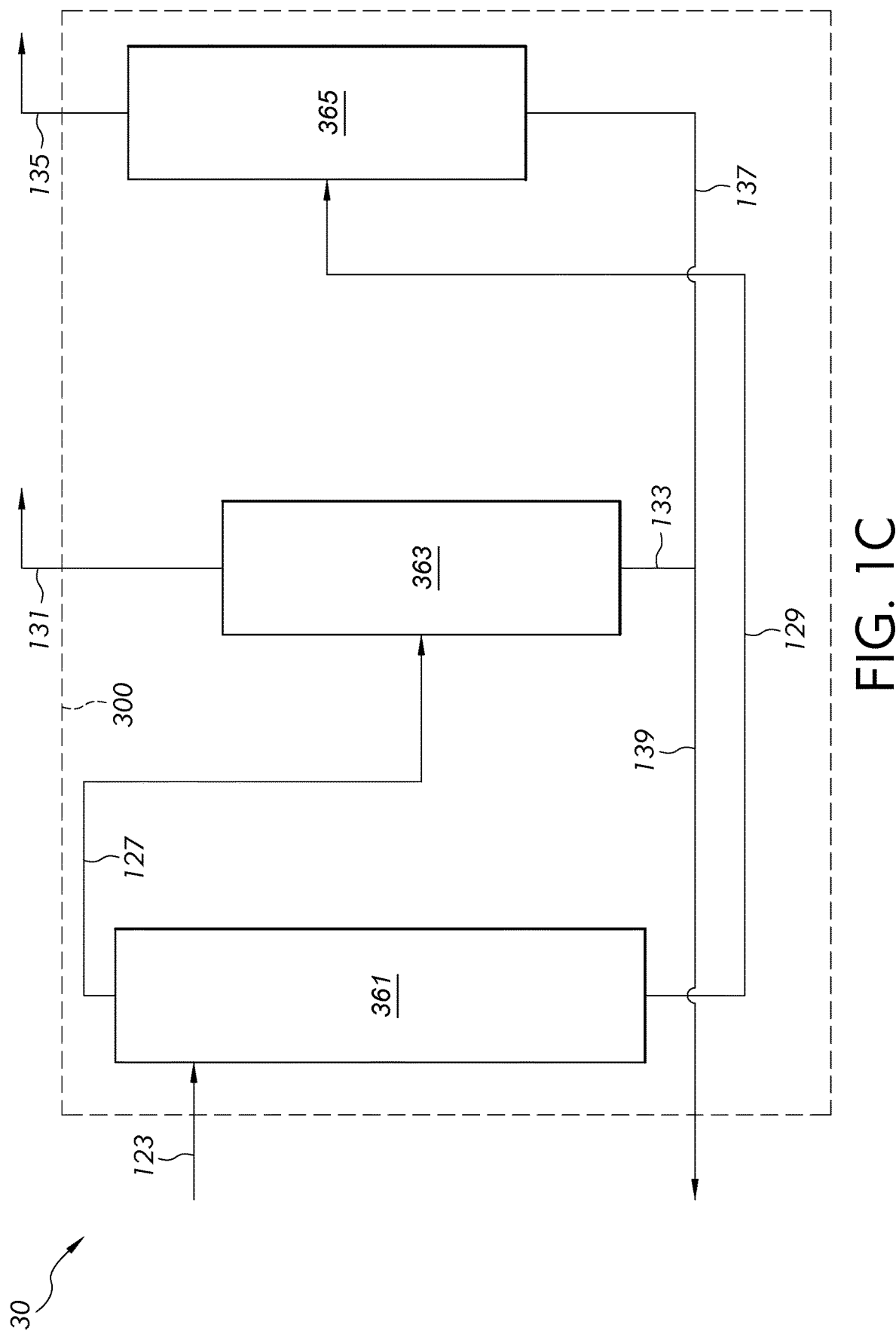
FIG. 1C schematically depicts a generalized flow diagram of an aromatics separation unit of the system of FIG. 1A, according to one or more embodiments shown and described in this disclosure.

Now referring to FIG. 1C, an embodiment of the BTX separation unit 300 as a separation system 30 that includes a solvent distillation column 361, a raffinate column 363, and a stripper column 365 is depicted. The separation system 30 can be applied to conduct distillation and recovering of BTX compounds as shown in FIG. 1C.

The solvent distillation column 361 may be in fluid communication with the gas/liquid separation unit 250 and may receive all or a portion of the liquid stream 123 from the gas/liquid separation unit 250. The solvent in the solvent distillation column 361 may comprise N-Methyl-2-pyrrolidone (NMP). In the presence of the solvent NMP, the BTX, aromatics and non-aromatics are separated in the solvent distillation column 361. Then, the non-aromatics with a small concentration of NMP solvent sent to the top of distillation column are transferred to the raffinate column 363 via line 127.

The raffinate column 363 may be in fluid communication with the solvent distillation column 361 and may receive all or a portion of line 127 containing the non-aromatics with a small concentration of NMP solvent from the solvent distillation column 361. In the raffinate column 363, the non-aromatics of alkanes and iso-alkanes are sent-out from the process via the unconverted aromatics stream 131. The recovered solvent is recycled again for further extraction via lines 133 and 139.

The stripper column 365 may be in fluid communication with the raffinate column 363 and may receive all or a portion of line 129 containing BTX and $C_{9+}$ aromatics along with at least some NMP solvent from the raffinate column 363. The BTX and $C_{9+}$ aromatics are separated from solvent under a vacuum and aromatics pass out of the unit via the aromatics effluent 135. The recovered solvent is recycled again for further extraction via lines 137 and 139.

In embodiments, the solvent distillation column 361 may operate at a temperature greater than or equal to 70° C. and less than or equal to 160° C. In embodiments, the solvent distillation column 361 may operate at a temperature greater than or equal to 80° C. and less than or equal to 141° C. In embodiments, the solvent distillation column 361 may operate at a temperature greater than or equal to 70° C., greater than or equal to 74° C., or even greater than or equal to 78° C. . . . In embodiments, the solvent distillation column 361 may operate at a temperature less than or equal to 160° C., less than or equal to 155° C., less than or equal to 150° C., or even less than or equal to 145° C. In embodiments, the solvent distillation column 361 may operate at a temperature greater than or equal to 70° C. and less than or equal to 74° C. greater than or equal to 74° C. and less than or equal to 78° C. greater than or equal to 78° C. and less than or equal to 145° C., greater than or equal to 145° C. and less than or equal to 150° C. greater than or equal to 150° C. and less than or equal to 155° C. greater than or equal to 155° C. and less than or equal to 160° C., or any and all sub-ranges formed from any of these endpoints.

In embodiments, the raffinate column 363 may operate at a temperature in the range of from greater than 141° C. and less than or equal to 250° C. In embodiments, the raffinate column 363 may operate at a temperature greater than or equal to 145° C. and less than or equal to 190° C. In embodiments, the raffinate column 363 may operate at a temperature greater than 141° C. or even greater than or equal to 145° C. In embodiments, the raffinate column 363 may operate at a temperature less than or equal to 250° C., less than or equal to 225° C., or even less than or equal to 200° C. In embodiments, the raffinate column 363 may operate at a temperature greater than or equal to 141° C. and less than or equal to 145° C., greater than or equal to 145° C. and less than or equal to 200° C., greater than or equal to 200° C. and less than or equal to 225° C., greater than or equal to 225° C. and less than or equal to 250° C., or any and all sub-ranges formed from any of these endpoints.

In embodiments, the stripper column 365 may operate at a temperature in the range of from greater than 180° C. and less than or equal to 290° C. In embodiments, the stripper column 365 may operate at a temperature greater than or equal to 200° C. and less than or equal to 290° C. In embodiments, the stripper column 365 may operate at a temperature greater than 180° C. greater than or equal to 190° C., or even greater than or equal to 200° C. In embodiments, the stripper column 365 may operate at a temperature less than or equal to 290° C. or even less than or equal to 285° C. In embodiments, the stripper column 365 may operate at a temperature greater than or equal to 180° C. and less than or equal to 190° C., greater than or equal to 190° C. and less than or equal to 200° C., greater than or equal to 200° C. and less than or equal to 285° C. greater than or equal to 285° C. and less than or equal to 290° C., or any and all sub-ranges formed from any of these endpoints.

In embodiments, the aromatics content, including BTX, of the aromatics effluent 135 may be greater than or equal to 5 wt. % and less than or equal to 50 wt. %. In embodiments, the aromatics content, including BTX, of the aromatics effluent 135 may be greater than or equal to 10 wt. % and less than or equal to 30 wt. %. In embodiments, the aromatics content, including BTX, of the aromatics effluent 135 may be greater than or equal to 5 wt. %, greater than or equal to 15 wt. %, or even greater than or equal to 25 wt. %. In embodiments, the aromatics content, including BTX, of the aromatics effluent 135 may be less than or equal to 50 wt. %, less than or equal to 40 wt. %, or even less than or equal to 30 wt. %. In embodiments, the aromatics content, including BTX, of the aromatics effluent 135 may be greater than or equal to 5 wt. % and less than or equal to 15 wt. %, greater than or equal to 15 wt. % and less than or equal to 25 wt. %, greater than or equal to 25 wt. % and less than or equal to 30 wt. %, greater than or equal to 30 wt. % and less than or equal to 40 wt. %, greater than or equal to 40 wt. % and less than or equal to 50 wt. %, or any and all sub-ranges formed from any of these endpoints.

In embodiments, the paraffin and isoparaffin content of the unconverted aromatics stream 131 in the system 101 may be greater than or equal to 10 wt. % and less than or equal to 60 wt. %. In embodiments, the paraffin and isoparaffin content of the unconverted aromatics stream 131 may be greater be greater than or equal to 10 wt. %, greater than or equal to 15 wt. %, or even greater than or equal to 25 wt. %. In embodiments, the paraffin and isoparaffin content of the unconverted aromatics stream 131 may be less than or equal to 60 wt. %, less than or equal to 50 wt. %, or even less than or equal to 40 wt. %. In embodiments, the paraffin and isoparaffin content of the unconverted aromatics stream 131 may be greater than or equal to 10 wt. % and less than or equal to 15 wt. %, greater than or equal to 15 wt. % and less than or equal to 25 wt. %, greater than or equal to 25 wt. % and less than or equal to 40 wt. %, greater than or equal to 40 wt. % and less than or equal to 50 wt. %, greater than or equal to 50 wt. % and less than or equal to 60 wt. %, or any and all sub-ranges formed from any of these endpoints.

Steam Cracking Unit

Referring again to FIG. 1A, the system 101 may include the steam cracking unit 500, which may be disposed downstream of the adsorption unit 100. The steam cracking unit 500 may be in fluid communication with the adsorption unit 100 and may receive all or a portion of the paraffins stream 107 from the adsorption unit 100.

The paraffins stream 107 may be passed directly from the adsorption unit 100 to the steam cracking unit 500 without passing through any intervening reactor or separation system. The steam cracking unit 500 may be operable to crack at least a portion of the paraffins stream 107 in the presence of at least one cracking catalyst to produce the ethylene stream 141.

The isoparaffin content in the naphtha feed 103 may hinder the ethylene yield in the steam cracking unit 500. Low ethylene yield also correlates with increased undesired byproducts including fuel gas, pyoil, and pygas during the steam cracking. To mitigate this issue, the steam cracking unit 500 may receive the paraffins stream 107. A feed comprising more paraffins produces a higher yield of ethylene and less byproducts.

In embodiments, the steam cracking unit 500 may operate at a temperature greater than or equal to 700° C. and less than or equal to 950° C. In embodiments, the steam cracking unit 500 may operate at a temperature greater than or equal to 850° C. and less than or equal to 900° C. In embodiments, the steam cracking unit 500 may operate at a temperature greater than or equal to 700° C., greater than or equal to 725° C., greater than or equal to 750° C., greater than or equal to 775° C., greater than or equal to 800° C., greater than or equal to 825° C., or even greater than or equal to 850° C. In embodiments, the steam cracking unit 500 may operate at a temperature of less than or equal to 950° C., less than or equal to 925° C., or even less than or equal to 900° C. In embodiments, the steam cracking unit 500 may operate at a temperature greater than or equal to 700° C. and less than or equal 725° C., greater than or equal to 725° C. and less than or equal to 750° C., greater than or equal to 750° C. and less than or equal to 775° C. greater than or equal to 775° C. and less than or equal 800° C., greater than or equal to 800° C. and less than or equal to 900° C. greater than or equal to 900° C. and less than or equal to 925° C. greater than or equal to 925° C. and less than or equal 950° C., or any and all sub-ranges formed from any of these endpoints.

In embodiments, the steam cracking unit 500 may operate at a pressure of from 0.1 MPa (1 bar) to 2 MPa (20 bar). In embodiments, the steam cracking unit 500 may operate at a pressure greater than or equal to 0.1 MPa and less than or equal to 0.5 MPa. In embodiments, the steam cracking unit 500 may operate at a pressure greater than or equal to 0.1 MPa or even greater than or equal to 0.15 MPa. In embodiments, the steam cracking unit 500 may operate at a pressure less than or equal to 2 MPa, less than or equal to 1.5 MPa, or even less than or equal to 1 MPa. In embodiments, the steam cracking unit 500 may operate at a pressure greater than or equal to 0.1 MPa and less or equal to 0.5 MPa, greater than or equal to 0.5 MPa and less than or equal to 1 MPa, greater than or equal to 1 MPa and less than or equal to 1.5 MPa, greater than or equal to 1.5 MPa and less or equal to 2 MPa, or any and all sub-ranges formed from any of these endpoints.

In embodiments, the ethylene content of the ethylene stream 141 may be greater than or equal to 30 wt. % and less than or equal to 55 wt. %. In embodiments, the ethylene content of the ethylene stream 141 may be greater than or equal to 35 wt. % to less than or equal to 45 wt. %. In embodiments, the ethylene content of the ethylene stream 141 may be greater than or equal to 30 wt. % or even greater than or equal to 35 wt. %. In embodiments, the ethylene content of the ethylene stream 141 may be less than or equal to 55 wt. %, less than or equal to 50 wt. %, or even less than or equal to 45 wt. %. In embodiments, the ethylene content of the ethylene stream 141 may be greater than or equal to 30 wt. % and less than or equal to 35 wt. %, greater than or equal to 35 wt. % and less than or equal to 45 wt. %, greater than or equal to 45 wt. % and less than or equal to 50 wt. %, greater than or equal to 50 wt. % and less than or equal to 55 wt. %, or any and all sub-ranges formed from any of these endpoints.

Gas Separation Unit

Still referring to FIG. 1A, the system 101 may include the gas separation unit 400, which may be disposed downstream of the gas/liquid separation unit 250 and the steam cracking unit 500. The gas separation unit 400 may be in fluid communication with the gas/liquid separation unit 250 and the steam cracking unit 500. The gas separation unit 400 may receive all or a portion of the gas stream 125 from the gas/liquid separation unit 250 and all or a portion of the ethylene stream 141 from the steam cracking unit 500.

The gas stream 125 and the ethylene stream 141 may be passed directly to the gas separation unit 400 without passing through any intervening reactor or separation system. The gas separation unit 400 may be operable to separate at least a portion of the gas stream 125 and the ethylene stream 141 into at least an olefins stream 143, a byproduct stream 145, and an aromatic-rich stream 147.

The gas separation unit 400 may operate at a temperature greater than or equal to 30° C. and less than or equal to 150° C. The gas separation unit 400 may operate at a pressure greater than or equal to 1 MPa (10 bar) to 2 MPa (20 bar). In embodiments, gas separation unit 400 may operate at a temperature greater than or equal to 30° C., greater than or equal to 35° C., or even greater than or equal to 40° C. In embodiments, gas separation unit 400 may operate at a temperature less than or equal to 150° C., less than or equal to 145° C., or even less than or equal to 140° C. In embodiments, the gas separation unit 400 may operate at a temperature greater than or equal to 30° C. and less than or equal to 35° C., greater than or equal to 35° C. and less than or equal to 40° C., greater than or equal to 40° C. and less than or equal to 140° C., greater than or equal to 140° C. and less than or equal to 145° C., greater than or equal to 145° C. and less than or equal to 150° C., or even greater than or equal to 40° C. and less than or equal to 140° C. or any and all sub-ranges formed from any of these endpoints. In embodiments, the gas separation unit 400 may operate at a pressure greater than or equal to 0.1 MPa, greater than or equal to 0.15 MPa, or even greater than or equal to 0.2 MPa. In embodiments, the gas separation unit 400 may operate at a pressure less than or equal to 20 MPa, less than or equal to 18 MPa, or even less than or equal to 16 MPa. In embodiments, the gas separation unit 400 may operate at a pressure greater than or equal to 0.1 MPa and less than or equal to 0.15 MPa, greater than or equal to 0.15 MPa and less than or equal to 0.2 MPa, greater than or equal to 0.2 MPa and less than or equal 16 MPa, greater than or equal to 16 MPa and less than or equal to 18 MPa, greater than or equal to 18 MPa and less than or equal to 20 MPa, or any and all sub-ranges formed from any of these endpoints.

In embodiments, the olefins content of the olefins stream 143 may be greater than or equal to 20 wt. % and less than or equal to 70 wt. %. In embodiments, the olefins content of the olefins stream 143 may be greater than or equal to 30 wt. % and less than or equal to 60 wt. %. In embodiments, the olefins content of the olefins stream 143 may be greater than or equal to 20 wt. %, greater than or equal to 25 wt. %, or even greater than or equal to 30 wt. %. In embodiments, the olefins content of the olefins stream 143 may be less than or equal 70 wt. %, less than or equal to 65 wt. %, or even less than or equal to 60 wt. %. In embodiments, the olefins content of the olefins stream 143 may be greater than or equal to 20 wt. % and less than or equal 25 wt. %, greater than or equal 25 wt. % and less than or equal to 30 wt. %, greater than or equal to 30 wt. % and less than or equal to 60 wt. %, greater than or equal to 60 wt. % and less than or equal 65 wt. %, greater than or equal 65 wt. % and less than or equal to 70 wt. %, or any and all sub-ranges formed from any of these endpoints.

In embodiments, the alkane content of the byproduct stream 145 may be greater than or equal to 20 wt. % and less than or equal to 50 wt. %. The alkane composition of the byproduct stream 145 may be 5-20 wt. % methane, 5-30 wt. % ethane, 5-30 wt. % propane, and 5-30 wt. % butane.

In embodiments, the aromatics content of the aromatic-rich stream 147 may be greater than or equal to 10 wt. % and less than or equal to 90 wt. %. In embodiments, the aromatics content of the aromatic-rich stream 147 may be greater than or equal to 10 wt. % and less than or equal to 30 wt. %. In embodiments, the aromatics content of the aromatic-rich stream 147 may be greater than or equal to 10 wt. %, greater than or equal to 20 wt. %, or even greater than or equal to 30 wt. %. In embodiments, the aromatics content of the aromatic-rich stream 147 may be less than or equal to 90 wt. %, less than or equal to 65 wt. %, or even less than or equal to 40 wt. %. In embodiments, the aromatics content of the aromatic-rich stream 147 may be greater than or equal to 10 wt. % and less than or equal to 20 wt. %, greater than or equal to 20 wt. % and less than or equal to 30 wt. %, greater than or equal to 30 wt. % and less than or equal to 40 wt. %, greater than or equal to 40 wt. % and less than or equal to 65 wt. %, greater than or equal to 65 wt. % and less than or equal to 90 wt. %, or any and all sub-ranges formed from any of these endpoints.

Configuration II

Figure 2:
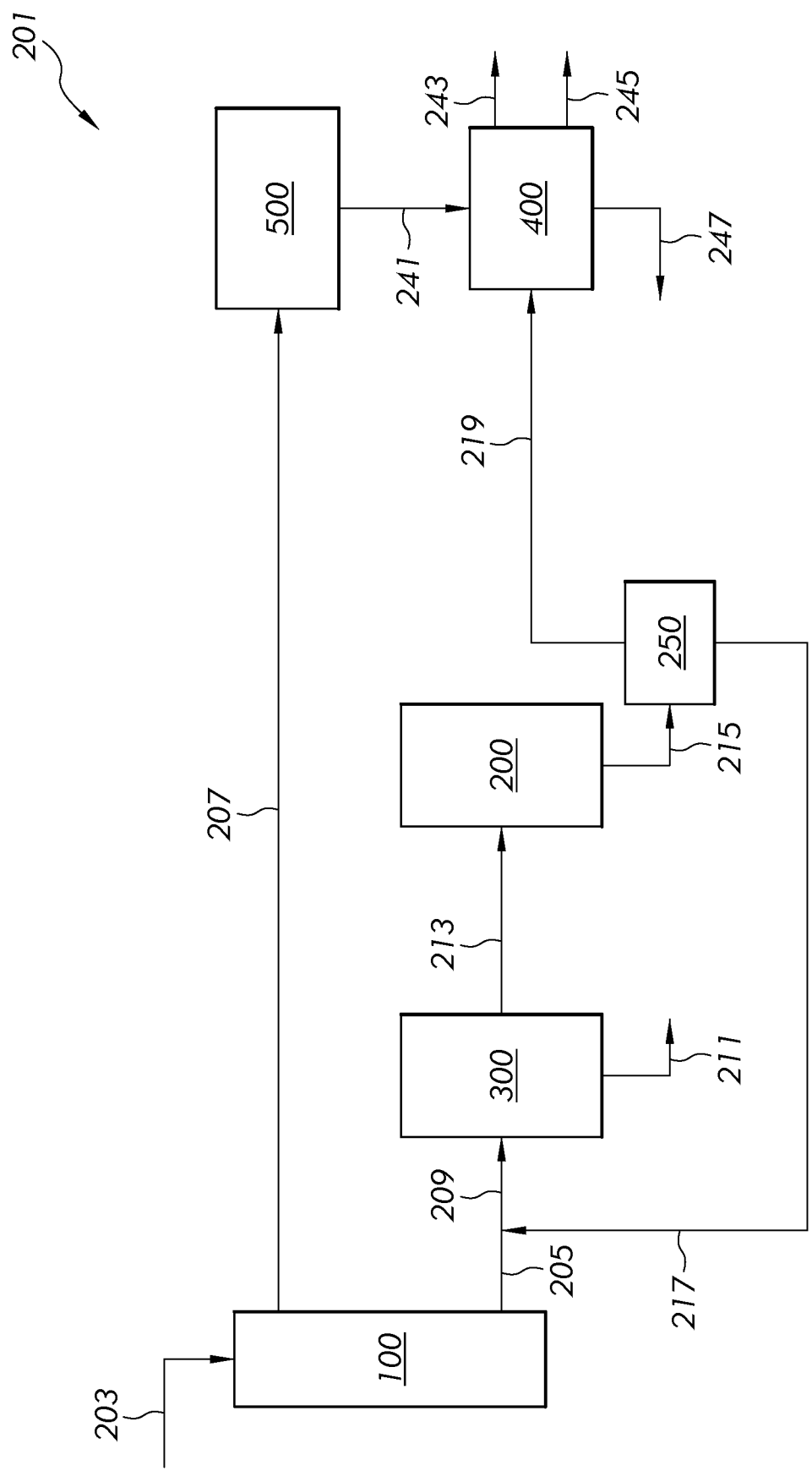
FIG. 2 schematically depicts a generalized flow diagram of a system for upgrading a naphtha feed, according to one or more embodiments shown and described in this disclosure.

Now referring to FIG. 2, a system 201 for upgrading a naphtha feed 203 is schematically depicted. Now referring to FIG. 2, in one or more embodiments, the system 201 for upgrading a naphtha feed may be substantially similar to the system 101 depicted in FIGS. 1A-1C. The difference between the system 201 depicted in FIG. 2 and the system 101 depicted in FIGS. 1A-1C is that Configuration II sends isoparaffins separated from the naphtha feed to the BTX separation unit 300 prior to the processing step involving the isoparaffin aromatization catalytic unit 200. Further, the liquid separated in the gas/liquid separation unit 250 is recycled back to the isoparaffins entering the BTX separation unit 300. This configuration may be beneficial for feeds that require handling of naphtha rich with isoparaffin content and aromatics because these compounds are separated before aromatization.

The system 201 may include an adsorption unit 100, a BTX separation unit 300 downstream of the adsorption unit 100, and a steam cracking unit 500 downstream of the adsorption unit 100. The adsorption unit 100 may be operable to contact the naphtha feed 203 into at least a paraffins stream 207 and an unmixed isoparaffins stream 205. The unmixed isoparaffins stream 205 may be mixed with a liquid stream 217 to form a mixed isoparaffins stream 209. The BTX separation unit 300 may be operable to separate the mixed isoparaffins stream 209 into at least an aromatics effluent 211 and an isoparaffins stream 213. The aromatics effluent 211 may comprise at least benzene, toluene, xylenes, and/or a combination of these. The isoparaffins stream 213 may comprise mostly non-aromatized isoparaffins.

Adsorption Unit

It will be appreciated by those skilled in the art that the boiling point may range between various operations and between various sources of the naphtha feed 203. The naphtha feed 203 may be a naphtha from any source. The naphtha feed 203 may comprise a straight run naphtha or an intermediate stream from any refinery process units. For example, the naphtha feed 103 may comprise a straight run naphtha from distillation or processing of crude oil. Additionally or alternatively, the naphtha feed 203 may include an intermediate naphtha stream from a coker, a visbreaker, or a hydrocracker. Other sources of naphtha streams are contemplated. In embodiments, the naphtha of the naphtha feed 203 may comprise light naphtha, whole naphtha, or a combination of both.

Still referring to FIG. 2, the isoparaffin content of the naphtha feed 203 may be greater than or equal to 20 wt. % and less than or equal to 40 wt. %. In embodiments, the isoparaffin content of the naphtha feed 203 may be greater than or equal to 20 wt. %, greater than or equal to 25 wt. %, or even greater than or equal to 30 wt. %. In embodiments, the isoparaffin content of the naphtha feed 203 may be less than or equal to 40 wt. % or even less than or equal to 35 wt. %. In embodiments, the isoparaffin content of the naphtha feed 203 may be greater than or equal to 20 wt. % and less than or equal to 25 wt. %, greater than or equal to 25 wt. % and less than or equal to 30 wt. %, greater than or equal to 30 wt. % and less than or equal to 35 wt. %, greater than or equal to 35 wt. % and less than or equal to 40 wt. %, or any and all sub-ranges formed from any of these endpoints.

In embodiments, the paraffin content of the naphtha feed 203 may be greater than or equal to 20 wt. % and less than or equal to 40 wt. %. In embodiments, the paraffin content of the naphtha feed 203 may be greater than or equal to 20 wt. %, greater than or equal to 25 wt. %, or even greater than or equal to 30 wt. %. In embodiments, the paraffin content of the naphtha feed 203 may be less than or equal to 40 wt. % or even less than or equal to 35 wt. %. In embodiments, the paraffin content of the naphtha feed 203 may be less than or equal to 40 wt. % or even less than or equal to 35 wt. %. In embodiments, the isoparaffin content of the naphtha feed 203 may be greater than or equal to 20 wt. % and less than or equal to 25 wt. %, greater than or equal to 25 wt. % and less than or equal to 30 wt. %, greater than or equal to 30 wt. % and less than or equal to 35 wt. %, greater than or equal to 35 wt. % and less than or equal to 40 wt. %, or any and all sub-ranges formed from any of these endpoints.

In embodiments, the aromatics content of the naphtha feed 203 in the system 201 may be greater than or equal to 10 wt. % and less than or equal to 50 wt. %. In embodiments, the aromatics content of the naphtha feed 203 in the system 201 may be greater than or equal to 10 wt. %, greater than or equal to 15 wt. %, or even greater than or equal to 20 wt. %. In embodiments, the aromatics content of the naphtha feed 203 in the system 201 may be less than or equal to 50 wt. %, less than or equal to 45 wt. %, or even less than or equal to 40 wt. %. In embodiments, the aromatics content of the naphtha feed 203 in the system 201 may be greater than or equal to 10 wt. % and less than or equal to 15 wt. %, greater than or equal to 15 wt. % and less than or equal to 20 wt. %, greater than or equal to 20 wt. % and less than or equal to 40 wt. %, greater than or equal to 40 wt. % and less than or equal to 45 wt. %, greater than or equal to 45 wt. % and less than or equal to 50 wt. %, or any and all sub-ranges formed from any of these endpoints.

In embodiments, the naphtha feed 203 may comprise a nominal boiling temperature greater than or equal to 30° C. and less than or equal to 157° C. In embodiments, the boiling temperature range of the naphtha feed 203 may be greater than or equal to 30° C., greater than or equal to 50° C., or even greater than or equal to 70° C. In embodiments, the boiling temperature range of the naphtha feed 203 may be less than or equal to 157° C., less than or equal to 130° C., or even less than or equal to 100° C. In embodiments, the boiling temperature range of the naphtha feed 203 may be greater than or equal to 30° C. and less than or equal to 50° C. greater than or equal to 50° C. and less than or equal to 70° C., greater than or equal to 70° C. and less than or equal to 100° C., greater than or equal to 100° C. and less than or equal to 130° C., greater than or equal to 130° C. and less than or equal to 157° C., or any and all sub-ranges formed from any of these endpoints.

In embodiments, sulfur components of naphtha feed 203 may be the same as the sulfur content of naphtha feed 103, greater than 0.1 parts per million by weight (ppmw) to less than or equal to 2000 ppmw.

In one embodiment, the naphtha feed 203 may be passed directly to the adsorption unit 100 without passing through any intervening reactor or separation system. The adsorption unit 100 may be in fluid communication with the BTX separation unit 300. The adsorption unit 100 may be operable to separate the naphtha feed 203 at least a paraffins stream 207 and an unmixed isoparaffins stream 205. The adsorption unit 100 may have any of the features or operating conditions previously described in the present disclosure for the adsorption unit 100.

In embodiments, the paraffin content of the paraffins stream 207 may be greater than or equal to 10 wt. % and less than or equal to 50 wt. %. In embodiments, the isoparaffins content of the paraffins stream 207 may be greater than or equal to 10 wt. %, greater than or equal to 20 wt. %, or even greater than or equal to 30 wt. %. In embodiments, the isoparaffins content of the paraffins stream 207 may be less than or equal to 50 wt. %, less than or equal to 45 wt. %, or even less than or equal to 40 wt. %. In embodiments, the isoparaffins content of the paraffins stream 207 may be greater than or equal to 10 wt. % and less than or equal to 20 wt. %, greater than or equal to 20 wt. % and less than or equal to 30 wt. %, greater than or equal to 30 wt. % and less than or equal to 40 wt. %, greater than or equal to 40 wt. % and less than or equal to 45 wt. %, greater than or equal to 45 wt. % and less than or equal to 50 wt. %, or any and all sub-ranges formed from any of these endpoints.

In embodiments, the isoparaffin content of the unmixed isoparaffins stream 205 may be greater than or equal to 5 wt. % and less than or equal to 45 wt. % isoparaffins. In embodiments, the isoparaffin content of the unmixed isoparaffins stream 205 may be greater than or equal to 15 wt. % and less than or equal to 35 wt. %. In embodiments, the isoparaffin content of the unmixed isoparaffins stream 205 may be greater than or equal to 5 wt. %, greater than or equal to 10 wt. %, or even greater than or equal to 15 wt. %. In embodiments, the isoparaffin content of the unmixed isoparaffins stream 205 may be less than or equal to 45 wt. %, less than or equal to 40 wt. %, or even less than or equal to 35 wt. %. The isoparaffin content of the unmixed isoparaffins stream 205 may be greater than or equal to 5 wt. % and less than or equal to 10 wt. %, greater than or equal to 10 wt. % and less than or equal to 15 wt. %, greater than or equal to 15 wt. % and less than or equal to 35 wt. %, greater than or equal to 35 wt. % and less than or equal to 40 wt. %, greater than or equal to 40 wt. % and less than or equal to 45 wt. %, or any and all sub-ranges formed from any of these endpoints.

BTX Separation Unit

Still referring to FIG. 2, the system 201 may include the BTX separation unit 300, which may be disposed downstream of the adsorption unit 100. The BTX separation unit 300 may be in fluid communication with the isoparaffin aromatization catalytic unit 200 and may receive all or a portion of the mixed isoparaffins stream 209. The BTX separation unit 300 may include one or a plurality of separation units. The BTX separation unit 300 may be part of the separation system 30 as depicted in FIG. 1C.

In embodiments, the isoparaffin content of the mixed isoparaffins stream 209 may be greater than or equal to 10 wt. % and less than or equal to 50 wt. %. In embodiments, the isoparaffin content of the mixed isoparaffins stream 209 may be greater than or equal to 10 wt. %, greater than or equal to 15 wt. %, or even greater than or equal to 20 wt. %. In embodiments, the isoparaffin content of the mixed isoparaffins stream 209 may be less than or equal to 50 wt. %, less than or equal to 40 wt. %, or even less than or equal to 30 wt. %. The isoparaffin content of the mixed isoparaffins stream 209 may be greater than or equal to 10 wt. % and less than or equal to 15 wt. %, greater than or equal to 15 wt. % and less than or equal to 20 wt. %, greater than or equal to 20 wt. % and less than or equal to 30 wt. %, greater than or equal to 30 wt. % and less than or equal to 40 wt. %, greater than or equal to 40 wt. % and less than or equal to 50 wt. %, or any and all sub-ranges formed from any of these endpoints.

In one embodiment, referring again to FIG. 2, the mixed isoparaffins stream 209 may be passed directly to the BTX separation unit 300 without passing through any intervening reactor or separation system. The BTX separation unit 300 may be operable to separate the mixed isoparaffins stream 209 into at least the aromatics effluent 211 and the isoparaffins stream 213. The aromatics effluent 211 may comprise at least benzene, toluene, xylenes, and/or a combination of these. The isoparaffins stream 213 may comprise at least some isoparaffins. The BTX separation unit 300 may have any of the features or operating conditions previously described in the present disclosure for the BTX separation unit 300.

In embodiments, the aromatics content, including BTX, of the aromatics effluent 211 in the system 201 may be greater than or equal to 20 wt. % and less than or equal to 90 wt. %. In embodiments, the aromatics content, including BTX, of the aromatics effluent 211 may be greater than or equal to 20 wt. %, greater than or equal to 30 wt. %, or even greater than or equal to 40 wt. %. In embodiments, the aromatics content, including BTX, of the aromatics effluent 211 may be less than or equal to 90 wt. %, less than or equal to 70 wt. %, or even less than or equal to 50 wt. %. The aromatics content, including BTX, of the aromatics effluent 211 may be greater than or equal to 20 wt. % and less than or equal to 30 wt. %, greater than or equal to 30 wt. % and less than or equal to 40 wt. %, greater than or equal to 40 wt. % and less than or equal to 50 wt. %, greater than or equal to 50 wt. % and less than or equal to 70 wt. %, greater than or equal to 50 wt. % and less than or equal to 70 wt. %, greater than or equal to 70 wt. % and less than or equal to 90 wt. %, or any and all sub-ranges formed from any of these endpoints.

In embodiments, the isoparaffin content of isoparaffins stream 213 in the system 201 may be greater than or equal to 20 wt. % and less than or equal to 60 wt. %. In embodiments, the isoparaffin content of isoparaffins stream 213 may be greater than or equal to 20 wt. %, greater than or equal to 25 wt. %, or greater than or equal to 30 wt. %. In embodiments, the isoparaffin content of isoparaffins stream 213 may be less than or equal to 60 wt. %, less than or equal to 50 wt. %, or less than or equal to 40 wt. %. In embodiments, the isoparaffin content of isoparaffins stream 213 may be greater than or equal to 20 wt. % and less than or equal to 25 wt. %, greater than or equal to 25 wt. % and less than or equal to 30 wt. %, greater than or equal to 30 wt. % and less than or equal to 40 wt. %, greater than or equal to 40 wt. % and less than or equal to 50 wt. %, greater than or equal to 50 wt. % and less than or equal to 60 wt. %, or any and all sub-ranges formed from any of these endpoints.

Isoparaffin Aromatization Catalytic Unit

Still referring to FIG. 2, the system 201 may include the isoparaffin aromatization catalytic unit 200, which may be disposed downstream of the BTX separation unit 300. The isoparaffin aromatization catalytic unit 200 may be part of an aromatization system 20 that includes a gas/liquid separation unit 250 in addition to the isoparaffin aromatization catalytic unit 200 as depicted in FIG. 1B. The isoparaffin aromatization catalytic unit 200 may be in fluid communication with the BTX separation unit 300 and may receive all or a portion of the isoparaffins stream 213 BTX separation unit 300 from the BTX separation unit 300

In one embodiment, again referring to FIG. 2, the isoparaffins stream 213 may be passed directly from the mixing of the liquid stream 217 and the unmixed isoparaffins stream 205 to the isoparaffin aromatization catalytic unit 200 without passing through any intervening reactor or separation system. The isoparaffin aromatization catalytic unit 200 may be operable to contact at least a portion of the isoparaffins stream 213 in the presence of at least one aromatization catalyst to produce an aromatization effluent 215. The isoparaffin aromatization catalytic unit 200 may have any of the features or operating conditions previously described in the present disclosure for the isoparaffin aromatization catalytic unit 200.

In embodiments, the aromatics content of aromatization effluent 215 in the system 201 may be greater than or equal to 20 wt. % and less than or equal to 90 wt. %. In embodiments, the aromatics content of the aromatization effluent 215 may be greater than or equal to 20 wt. %, greater than or equal to 30 wt. %, or even greater than or equal to 40 wt. %. In embodiments, the aromatics content of the aromatization effluent 121 may be less than or equal to 90 wt. %, less than or equal 80 wt. %, or even less than or equal to 70 wt. %. In embodiments, the aromatics content of the aromatization effluent 121 may be greater than or equal to 20 wt. % and less than or equal to 30 wt. %, greater than or equal to 30 wt. % and less than or equal to 40 wt. %, greater than or equal to 40 wt. % and less than or equal to 70 wt. %, greater than or equal to 70 wt. % and less than or equal to 80 wt. %, greater than or equal to 80 wt. % and less than or equal to 90 wt. %, or any and all sub-ranges formed from any of these endpoints.

Gas/Liquid Separation Unit

Still referring to FIG. 2, the system 201 may include the gas/liquid separation unit 250, which may be disposed downstream of the isoparaffin aromatization catalytic unit 200. The gas/liquid separation unit 250 may be in fluid communication with the isoparaffin aromatization catalytic unit 200 and may receive all or a portion of the aromatization effluent 215 from the isoparaffin aromatization catalytic unit 200. The gas/liquid separation unit 250 may include one or a plurality of separation units.

In one embodiment, the aromatization effluent 215 may be passed directly from the isoparaffin aromatization catalytic unit 200 to gas/liquid separation unit 250 without passing through any intervening reactor or separation system. The gas/liquid separation unit 250 may be operable to separate the aromatization effluent 215 into at least the gas stream 219 and the liquid stream 217. The gas/liquid separation unit 250 may have any of the features or operating conditions previously described in the present disclosure for the gas/liquid separation unit 250.

In embodiments, the contents of the gas stream 219 in the system 201 may be alkanes and some light olefins separated from the aromatization effluent 215. The alkane composition of the gas stream 219 may be 1-20 wt. % methane, 1-30 wt. % ethane, 10-40 wt. % propane, 10-30 wt. % butane, and 1-5 wt. % pentane. The light olefins content may be from 1-15 wt. %.

In embodiments, the aromatics content of the liquid stream 217 in the system 201 may be greater than or equal to 60 wt. % and less than or equal to 95 wt. %. In embodiments, the aromatics content of the liquid stream 217 may be greater than or equal to 60 wt. %, greater than or equal to 65 wt. %, or greater than or equal to 70 wt. %. In embodiments, the aromatics content of the liquid stream 217 may be less than or equal to 95 wt. %, less than or equal to 85 wt. %, or less than or equal to 75 wt. %. In embodiments, the aromatics content of the liquid stream 217 may be greater than or equal to 60 wt. % and less than or equal to 65 wt. %, greater than or equal to 65 wt. % and less than or equal to 70 wt. %, greater than or equal to 70 wt. % and less than or equal to 75 wt. %, greater than or equal to 75 wt. % and less than or equal to 85 wt. %, greater than or equal to 85 wt. % and less than or equal to 95 wt. %, or any and all sub-ranges formed from any of these endpoints.

Steam Cracking Unit

Still referring to FIG. 2, the system 201 may include the steam cracking unit 500, which may be disposed downstream of the adsorption unit 100. The steam cracking unit 500 may be in fluid communication with the adsorption unit 100 and may receive all or a portion of the paraffins stream 207 from the adsorption unit 100.

In one embodiment, the paraffins stream 207 may be passed directly from the adsorption unit 100 to the steam cracking unit 500 without passing through any intervening reactor or separation system. The steam cracking unit 500 may be operable to crack at least a portion of the paraffins stream 207 in the presence of at least one cracking catalyst to produce an ethylene stream 241. The steam cracking unit 500 may have any of the features or operating conditions previously described in the present disclosure for the steam cracking unit 500.

In embodiments, the ethylene content of the ethylene stream 241 may be greater than or equal to 10 wt. % and less than or equal to 45 wt. %. In embodiments, the ethylene content of the ethylene stream 241 may be greater than or equal to 10 wt. % or even greater than or equal to 25 wt. %. In embodiments, the ethylene content of the ethylene stream 241 may be less than or equal to 45 wt. %, less than or equal to 40 wt. %, or even less than or equal to 35 wt. %. In embodiments, the ethylene content of the ethylene stream 241 may be greater than or equal to 10 wt. % and less than or equal to 25 wt. %, greater than or equal to 25 wt. % and less than or equal to 35 wt. %, greater than or equal to 35 wt. % and less than or equal to 40 wt. %, greater than or equal to 40 wt. % and less than or equal to 45 wt. %, or any and all sub-ranges formed from any of these endpoints.

Gas Separation Unit

Still referring to FIG. 2, the system 201 may include the gas separation unit 400, which may be disposed downstream of the gas/liquid separation unit 250 and the steam cracking unit 500. The gas separation unit 400 may be in fluid communication with the gas/liquid separation unit 250 and the steam cracking unit 500. The gas separation unit 400 may receive all or a portion of the gas stream 219 from the gas/liquid separation unit 250 and all or a portion of the ethylene stream 241 from the steam cracking unit 500.

In one embodiment, the gas stream 219 and the ethylene stream 241 may be passed directly from the gas/liquid separation unit 250 and the steam cracking unit 500 to the gas separation unit 400 without passing through any intervening reactor or separation system. The gas separation unit 400 may be operable to separate at least a portion of the gas stream 219 and the ethylene stream 241 into at least an olefins stream 243, a byproduct stream 245, and an aromatic-rich stream 247. The gas separation unit 400 may have any of the features or operating conditions previously described in the present disclosure for the gas separation unit 400.

In embodiments, the contents of the olefins stream 243 in the system 201 may be mostly olefins. The olefin composition of the olefins stream 243 may be 10-45 wt. % ethylene, 10-45 wt. % propylene, 10-45 wt. % butene, or any combination of these.

In embodiments, the byproduct stream 245 may comprise unreacted alkanes, paraffins, and isoparaffins. The composition of the byproduct stream 245 may be 5-25 wt. % methane, 5-35 wt. % ethane, 5-35 wt. % propane, 5-35 wt. % butane, 1-30 wt. % paraffins, 1-30 wt. % isoparaffins, or any combination of these.

In embodiments, the aromatics content of the aromatic-rich stream 247 may be greater than or equal to 20 wt. % and less than or equal to 90 wt. %. In embodiments, the aromatics content of the aromatic-rich stream 247 may be greater than or equal to 20 wt. %, greater than or equal to 25 wt. %, or even greater than or equal to 30 wt. %. In embodiments, the aromatics content of the aromatic-rich stream 247 may be less than or equal to 90 wt. %, less than or equal 70 wt. %, or even less than or equal to 50 wt. %. In embodiments, the aromatics content of the aromatic-rich stream 247 may be greater than or equal to 20 wt. % and less than or equal to 25 wt. %, greater than or equal to 25 wt. % and less than or equal to 30 wt. %, greater than or equal to 30 wt. % and less than or equal to 50 wt. %, greater than or equal to 50 wt. % and less than or equal to 70 wt. %, greater than or equal to 70 wt. % and less than or equal to 90 wt. %, or any and all sub-ranges formed from any of these endpoints.

Configuration III

Figure 3:
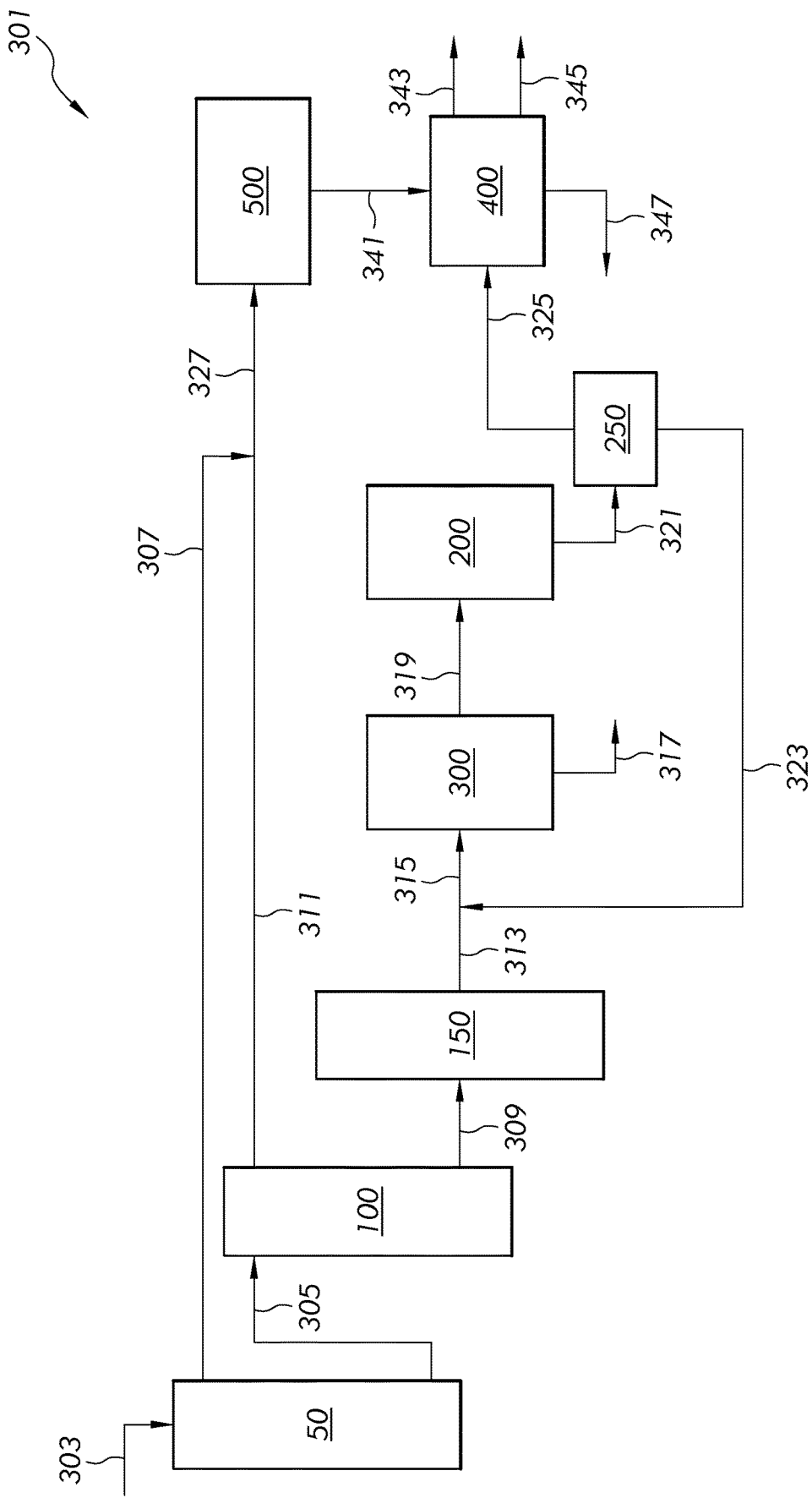
FIG. 3 schematically depicts a generalized flow diagram of a system for upgrading a naphtha feed, according to one or more embodiments shown and described in this disclosure.

Now referring to FIG. 3, a system 301 for upgrading a naphtha feed 303 is schematically depicted. In one or more embodiments, the system 301 for upgrading a naphtha feed may be substantially similar to the system 201 depicted in FIG. 2. The difference between the system 301 depicted in FIG. 3 and the system 201 depicted in FIG. 2 is that Configuration III includes a splitter unit 50 and a reforming unit 150. The splitter unit 50 allows for separation before adsorption, and the reforming unit 150 upgrades the isoparaffins of naphtha prior to BTX separation and adsorption. This configuration may be beneficial for feeds that require handling of straight run naphtha from crude oil with isoparaffins, naphthenes, and aromatics.

The system 301 may include the splitter unit 50, an adsorption unit 100 downstream of the splitter unit 50, a reforming unit 150 downstream of the adsorption unit 100, a BTX separation unit downstream of the reforming unit 150, and a steam cracking unit 500 downstream of the adsorption unit 100. The splitter unit 50 may be operable to separate the naphtha feed 303 into at least a high temperature stream 305 and a low temperature stream 307. The adsorption unit 100 may be operable to contact the high temperature stream 305 into at least a paraffins stream 311 and an unmixed isoparaffins stream 309. The low temperature stream 307 may be mixed with the paraffins stream 311 from the adsorption unit 100 to form a mixed paraffins stream 327. The reforming unit 150 may be operable to contact the unmixed isoparaffins stream 309 in the reforming unit 150 to produce a reformate 313. The reformate 313 may be mixed with a liquid stream 323 to form a mixed isoparaffins stream 315. The BTX separation unit 300 may be operable to separate the mixed isoparaffins stream 315 into at least an aromatics effluent 317 and an isoparaffins stream 319. The aromatics effluent 317 may comprise at least benzene, toluene, xylenes, and/or a combination of these. The liquid stream 323 may comprise mostly non-aromatized isoparaffins.

The system 301 may further include an isoparaffin aromatization catalytic unit 200 downstream of the BTX separation unit 300, a gas/liquid separation unit 250 downstream of the isoparaffin aromatization catalytic unit 200 and a gas separation unit 400 downstream of the gas/liquid separation unit 250. The isoparaffin aromatization catalytic unit 200 may be operable to contact the isoparaffins stream 319 in the presence of at least one aromatization catalyst. Contacting the isoparaffins stream 319 in the presence of at least one aromatization catalyst may produce an aromatization effluent 321 having a greater concentration of aromatics compared to the isoparaffins stream 319.

The system 301 may further include a gas/liquid separation unit 250 downstream of the isoparaffin aromatization catalytic unit 200. The gas/liquid separation unit 250 may be operable to separate the aromatization effluent 321 into the liquid stream 323 and a gas stream 325. The liquid stream 323 may be recycled and mixed with the reformate 313 to form a mixed isoparaffins stream 315.

The steam cracking unit 500 may be operable to contact the mixed paraffins stream 327 into at least an ethylene stream 341. The gas separation unit 400 is also downstream of the of the steam cracking unit 500. The gas separation unit 400 is operable to contact the ethylene stream 341 and the gas stream 325 into at least an olefins stream 343, a byproduct stream 345, and an aromatic-rich stream 347.

Splitter Unit

Still referring to FIG. 3, the naphtha feed 303 in the system 301 may comprise isoparaffins, paraffins, naphthenes, and at least some benzene, toluene, and/or xylenes (BTX) in an aromatics fraction.

In embodiments, the isoparaffin content of naphtha feed 303 may be greater than or equal to 20 wt. % and less than or equal to 35 wt. %. In embodiments, the isoparaffin content of naphtha feed 303 may be greater than or equal to 20 wt. %, greater than or equal to 21 wt. %, or even greater than or equal to 22 wt. %. In embodiments, the isoparaffin content of naphtha feed 303 may be less than or equal to 35 wt. %, less than or equal to 32 wt. %, or even less than or equal to 30 wt. %. In embodiments, the isoparaffin content of naphtha feed 303 may be greater than or equal to 20 wt. % and less than or equal to 21 wt. %, greater than or equal to 21 wt. % and less than or equal to 22 wt. %, greater than or equal to 22 wt. % and less than or equal to 30 wt. %, greater than or equal to 30 wt. % and less than or equal to 32 wt. %, greater than or equal to 32 wt. % and less than or equal to 35 wt. %, or any and all sub-ranges formed from any of these endpoints.

In embodiments, the paraffin content of naphtha feed 303 may be greater than or equal to 20 wt. % and less than or equal to 35 wt. %. In embodiments, the paraffin content of naphtha feed 303 may be greater than or equal to 20 wt. %, greater than or equal to 21 wt. %, or even greater than or equal to 22 wt. %. In embodiments, the paraffin content of naphtha feed 303 may be less than or equal to 35 wt. %, less than or equal to 32 wt. %, or even less than or equal to 30 wt. %. In embodiments, the paraffin content of naphtha feed 303 may be greater than or equal to 20 wt. % and less than or equal to 21 wt. %, greater than or equal to 21 wt. % and less than or equal to 22 wt. %, greater than or equal to 22 wt. % and less than or equal to 30 wt. %, greater than or equal to 30 wt. % and less than or equal to 32 wt. %, greater than or equal to 32 wt. % and less than or equal to 35 wt. %, or any and all sub-ranges formed from any of these endpoints.

In embodiments, the napthene content of naphtha feed 303 may be greater than or equal to 20 wt. % and less than or equal to 40 wt. %. In embodiments, the napthene content of naphtha feed 303 may be greater than or equal to 20 wt. % and less than or equal to 30 wt. %. In embodiments, the napthene content of naphtha feed 303 may be greater than or equal to 20 wt. %, greater than or equal to 21 wt. %, or even greater than or equal to 22 wt. %. In embodiments, the napthene content of naphtha feed 303 may be less than or equal to 40 wt. %, less than or equal to 35 wt. %, or even less than or equal to 30 wt. %. In embodiments, the paraffin content of naphtha feed 303 may be greater than or equal to 20 wt. % and less than or equal to 21 wt. %, greater than or equal to 21 wt. % and less than or equal to 22 wt. %, greater than or equal to 22 wt. % and less than or equal to 30 wt. %, greater than or equal to 30 wt. % and less than or equal to 35 wt. %, greater than or equal to 35 wt. % and less than or equal to 40 wt. %, or any and all sub-ranges formed from any of these endpoints.

In embodiments, the aromatics content of the naphtha feed 303 may be greater than or equal to 0.5 wt. % and less than or equal to 10 wt. %. In embodiments, the aromatics content of the naphtha feed 303 may be greater than or equal to 0.5 wt. %, greater than or equal to 1 wt. %, or even greater than or equal to 2 wt. %. In embodiments, the aromatics content of the naphtha feed 303 may be less than or equal to 10 wt. %, less than or equal to 8 wt. %, or even less than or equal to 6 wt. %. In embodiments, the aromatics content of the naphtha feed 303 may be greater than or equal to 0.5 wt. % and less than or equal to 1 wt. %, greater than or equal to 1 wt. % and less than or equal to 2 wt. %, greater than or equal to 2 wt. % and less than or equal to 6 wt. %, greater than or equal to 6 wt. % and less than or equal to 8 wt. %, greater than or equal to 8 wt. % and less than or equal to 10 wt. %, or any and all sub-ranges formed from any of these endpoints.

In embodiments, the naphtha feed 303 may comprise a nominal boiling temperature greater than or equal to 35° C. and less than or equal to 220° C. In embodiments, the boiling temperature range of the naphtha feed 303 may be greater than or equal to 35° C. greater than or equal to 55° C., or even greater than or equal to 75° C. In embodiments, the boiling temperature range of the naphtha feed 303 may be less than or equal to 220° C., less than or equal to 200° C. or even less than or equal to 180° C. In embodiments, the boiling temperature range of the naphtha feed 303 may be greater than or equal to 35° C. and less than or equal to 55° C., greater than or equal to 55° C. and less than or equal to 75° C., greater than or equal to 75° C. and less than or equal to 180° C., greater than or equal to 180° C. and less than or equal to 200° C., greater than or equal to 200° C. and less than or equal to 220° C., or any and all sub-ranges formed from any of these endpoints.

In embodiments, sulfur components of naphtha feed 303 may be the same as the sulfur content of naphtha feeds 103 and 203, greater than 0.1 parts per million by weight (ppmw) to less than or equal to 2000 ppmw.

It will be appreciated by those skilled in the art that the boiling point may range between various operations and between various sources of the naphtha feed 303. The naphtha feed 303 may be a naphtha from any source. The naphtha feed 303 may comprise a straight run naphtha or an intermediate stream from any refinery process units. For example, the naphtha feed 303 may comprise a straight run naphtha from distillation or processing of crude oil. Additionally or alternatively, the naphtha feed 303 may include an intermediate naphtha stream from a coker, a visbreaker, or a hydrocracker. Other sources of naphtha streams are contemplated.

In one embodiment, referring again to FIG. 3, the naphtha feed 303 may be passed directly to the splitter unit 50 without passing through any intervening reactor or separation system. The splitter unit 50 may be operable to separate the naphtha feed 303 into at least a high temperature stream 305 and a low temperature stream 307.

In embodiments, the splitter unit 50 may operate at a temperature greater than or equal to 30° C. and less than or equal to 110° C. In embodiments, the splitter unit 50 may operate at a pressure greater than or equal to 0.1 MPa (1 bar) and less than or equal to 1 MPa (10 bar). In embodiments, the splitter unit 50 may operate at a temperature greater than or equal to 36.1° C. and less than or equal to 98.4° C. In embodiments, the splitter unit 50 may operate at a temperature greater than or equal to 30° C., greater than or equal to 32° C., or even greater than or equal to 34° C. In embodiments, the splitter unit 50 may operate at a temperature less than or equal to 110° C. less than or equal to 105° C., or even less than or equal to 100° C. In embodiments, the splitter unit 50 may operate at a temperature greater than or equal to 30° C. and less than or equal to 32° C., greater than or equal to 32° C. and less than or equal to 34° C., greater than or equal to 34° C. and less than or equal to 100° C., greater than or equal to 100° C. and less than or equal to 105° C., greater than or equal to 105° C. and less than or equal to 110° C. or any and all sub-ranges formed from any of these endpoints. In embodiments, the splitter unit 50 may operate at a pressure greater than or equal to 0.1 MPa and less than or equal to 0.5 MPa. In embodiments, the splitter unit 50 may operate at a pressure greater than or equal to 0.1 MPa or even greater than or equal to 0.2 MPa. In embodiments, the splitter unit 50 may operate at a pressure less than or equal to 0.5 MPa or even and less than or equal to 0.4 MPa. In embodiments, the splitter unit 50 may operate at a pressure greater than or equal to 0.1 MPa and less than or equal to 0.2 MPa, greater than or equal to 0.2 MPa and less than or equal to 0.4 MPa, greater than or equal to 0.4 MPa and less than or equal to 0.5 MPa, or any and all sub-ranges formed from any of these endpoints.

In embodiments, the mid and heavy naphtha content of the high temperature stream 305 may be greater than or equal to 70 wt. % and less than or equal to 95 wt. %. In embodiments, the mid and heavy naphtha content of the high temperature stream 305 may be greater than or equal to 80 wt. % and less than or equal to 90 wt. %. In embodiments, the mid and heavy naphtha content of the high temperature stream 305 may be greater than or equal to 70 wt. %, greater than or equal to 75 wt. %, or even greater than or equal to 80 wt. %. In embodiments, the mid and heavy naphtha content of the high temperature stream 305 may be less than or equal to 95 wt. %, less than or equal to 92 wt. %, or even less than or equal to 90 wt. %. In embodiments, the mid and heavy naphtha content of the high temperature stream 305 may be greater than or equal to 70 wt. % and less than or equal to 75 wt. %, greater than or equal to 75 wt. % and less than or equal to 80 wt. %, greater than or equal to 80 wt. % and less than or equal to 90 wt. %, greater than or equal to 90 wt. % and less than or equal to 92 wt. %, greater than or equal to 92 wt. % and less than or equal to 95 wt. %, or any and all sub-ranges formed from any of these endpoints.

In embodiments, the light naphtha and light paraffin content of the low temperature stream 307 may be greater than or equal to 2 wt. % and less than or equal to 30 wt. %. In embodiments, the light naphtha and light paraffin content of the low temperature stream 307 may be greater than or equal to 5 wt. % and less than or equal to 10 wt. %. In embodiments, the light naphtha and light paraffin content of the low temperature stream 307 may be greater than or equal to 2 wt. %, greater than or equal to 3 wt. %, greater than or equal to 4 wt. %, or even greater than or equal to 5 wt. %. In embodiments, the light naphtha and light paraffin content of the low temperature stream 307 may be less than or equal to 30 wt. %, less than or equal to 20 wt. %, or even less than or equal to 10 wt. %. In embodiments, the light naphtha and light paraffin content of the low temperature stream 307 may be greater than or equal to 2 wt. % and less than or equal to 3 wt. %, greater than or equal to 3 wt. % and less than or equal to 4 wt. %, greater than or equal to 4 wt. % and less than or equal 5 wt. %, greater than or equal to 5 wt. % and less than or equal to 10 wt %., greater than or equal to 10 wt. % and less than or equal to 20 wt. %, greater than or equal to 20 wt. % and less than or equal 30 wt. %, or any and all sub-ranges formed from any of these endpoints.

Adsorption Unit

Still referring to FIG. 3, the high temperature stream 305 may be passed directly to the adsorption unit 100 without passing through any intervening reactor or separation system. The adsorption unit 100 may be in fluid communication with the reforming unit 150. The adsorption unit 100 may be operable to separate the high temperature stream 305 into at least the paraffins stream 311 and the unmixed isoparaffins stream 309. The adsorption unit 100 may have any of the features or operating conditions previously described in the present disclosure for the adsorption unit 100.

In embodiments, the isoparaffin content of the unmixed isoparaffins stream 309 may be greater than or equal to 5 wt. % and less than or equal to 45 wt. % isoparaffins. In embodiments, the isoparaffin content of the unmixed isoparaffins stream 309 may be greater than or equal to 15 wt. % and less than or equal to 35 wt. %. In embodiments, the isoparaffin content of the unmixed isoparaffins stream 309 may be greater than or equal to 5 wt. %, greater than or equal to 10 wt. %, or even greater than or equal to 15 wt. %. In embodiments, the isoparaffin content of the unmixed isoparaffins stream 309 may be less than or equal to 45 wt. %, less than or equal to 40 wt. %, or even less than or equal to 35 wt. %. The isoparaffin content of the unmixed isoparaffins stream 309 may be greater than or equal to 5 wt. % and less than or equal to 10 wt. %, greater than or equal to 10 wt. % and less than or equal to 15 wt. %, greater than or equal to 15 wt. % and less than or equal to 35 wt. %, greater than or equal to 35 wt. % and less than or equal to 40 wt. %, greater than or equal to 40 wt. % and less than or equal to 45 wt. %, or any and all sub-ranges formed from any of these endpoints.

In embodiments, the paraffin content of the paraffins stream 311 may be greater than or equal to 60 wt. % and less than or equal to 90 wt. %. In embodiments, the paraffin content of the paraffins stream 311 may be greater than or equal to 60 wt. %, greater than or equal to 65 wt. %, or even greater than or equal to 70 wt. %. In embodiments, the paraffin content of the paraffins stream 311 may be less than or equal to 90 wt. %, less than or equal to 85 wt. %, or even less than or equal to 80 wt. %. In embodiments, the paraffin content of the paraffins stream 311 may be greater than or equal to 60 wt. % and less than or equal to 65 wt. %, greater than or equal to 65 wt. % and less than or equal to 70 wt. %, greater than or equal to 70 wt. % and less than or equal to 80 wt. %, greater than or equal to 80 wt. % and less than or equal to 85 wt. %, greater than or equal to 85 wt. % and less than or equal to 90 wt. %, or any and all sub-ranges formed from any of these endpoints.

In embodiments, the isoparaffin content of the unmixed isoparaffins stream 309 may be greater than or equal to 25 wt. % and less than or equal to 45 wt. %. In embodiments, the isoparaffin content of the unmixed isoparaffins stream 309 may be greater than or equal to 25 wt. %, greater than or equal to 30 wt. %, or even greater than or equal to 35 wt. %. In embodiments, the isoparaffin content of the unmixed isoparaffins stream 309 may be less than or equal to 45 wt. %, or even less than or equal to 40 wt. %. In embodiments, the isoparaffin content of the unmixed isoparaffins stream 309 may be greater than or equal to 25 wt. % and less than or equal to 30 wt. %, greater than or equal to 30 wt. % and less than or equal to 35 wt. %, greater than or equal to 35 wt. % and less than or equal to 40 wt. %, greater than or equal to 40 wt. % and less than or equal to 45 wt. %, or any and all sub-ranges formed from any of these endpoints.

Reforming Unit

Still referring to FIG. 3, the unmixed isoparaffins stream 309 may be passed directly to the reforming unit 150 without passing through any intervening reactor or separation system. The reforming unit 150 may be in fluid communication with the BTX separation unit 300. The reforming unit 150 may be operable reform the unmixed isoparaffins stream 309 to produce a reformate 313. The unmixed isoparaffins stream 309 may be passed to the reforming unit 150 to upgrade the unmixed isoparaffins stream 309 to improve its quality, such as by increasing the octane number to produce the reformate 313.

The reforming unit 150 may be a catalytic reforming process. In catalytic reforming processes, paraffins and naphthenes can be restructured to produce isomerized paraffins and aromatics of relatively higher octane numbers. Catalytic reforming can convert low octane n-paraffins to i-paraffins and naphthenes. Naphthenes can then be converted to higher octane aromatic compounds. The chemical reactions involved in catalytic reforming can be grouped into four categories, which include cracking, dehydrocyclization, dehydrogenation, and isomerization. A particular hydrocarbon molecule of the unmixed isoparaffins stream 309 may undergo one or more than one category of reaction during the reforming process to form one or a plurality of different molecules or products. The reforming unit 150 may contact the unmixed isoparaffins stream 309 with a reforming catalyst under operating conditions sufficient to cause at least a portion of the unmixed isoparaffins stream 309 to undergo one or more reactions to produce a reformate 313.

In embodiments, the reforming unit 150 may operate at a temperature greater than or equal to 350° C. and less than or equal to 550° C. In embodiments, the reforming unit 150 may operate at a pressure greater than or equal to 0.5 MPa (5 bar) and less than or equal to 5 MPa (50 bar). In embodiments, the reforming unit 150 may operate at a temperature greater than or equal to 400° C. and less than or equal to 490° C. In embodiments, the reforming unit 150 may operate at a temperature greater than or equal to 350° C., greater than or equal to 375° C., or even greater than or equal to 400° C. In embodiments, the reforming unit 150 may operate at a temperature less than or equal to 550° C., less than or equal to 520° C., or even less than or equal to 490° C. In embodiments, the reforming unit 150 may operate at a temperature greater than or equal to 350° C. and less than or equal to 375° C. greater than or equal to 375° C. and less than or equal to 400° C., greater than or equal to 400° C. and less than or equal to 490° C., temperature greater than or equal to 490° C. and less than or equal to 520° C., greater than or equal to 520° C. and less than or equal to 550° C., or any and all sub-ranges formed from any of these endpoints. In embodiments, the reforming unit may operate at a pressure greater than or equal to 0.8 MPa and less than or equal to 2.5 MPa. In embodiments, the reforming unit 150 may operate at a pressure greater than or equal to 0.5 MPa, greater than or equal to 0.6 MPa, greater than or equal to 0.7 MPa, or even greater than or equal to 0.8 MPa. In embodiments, the reforming unit 150 may operate at a pressure less than or equal to 5 MPa, less than or equal to 4 MPa, or even less than or equal to 3 MPa. In embodiments, the reforming unit 150 may operate at a pressure greater than or equal to 0.5 MPa and less than or equal to 0.6 MPa, greater than or equal to 0.6 MPa and less than or equal to 0.7 MPa, greater than or equal to 0.7 MPa and less than or equal to 0.8 MPa, greater than or equal to 0.8 MPa and less than or equal to 3 MPa, greater than or equal to 3 MPa and less than or equal to 4 MPa, greater than or equal to 4 MPa and less than or equal to 5 MPa. or any and all sub-ranges formed from any of these endpoints.

In embodiments, the reforming unit 150 may operate at a liquid hourly space velocity (LHSV) greater than or equal to $0.1\ h^{-1}$ and less than or equal to $30\ h^{-1}$. In embodiments, the reforming unit 150 may operate at an LHSV greater than or equal to $0.5\ h^{-1}$ and less than or equal to $10\ h^{-1}$. In embodiments, the reforming unit 150 may operate at an LHSV greater than or equal to $0.1\ h^{-1}$, greater than or equal to $0.25\ h^{-1}$, or even greater than or equal to $0.5\ h^{-1}$. In embodiments, reforming unit 150 may operate at an LHSV less than or equal to $30\ h^{-1}$, less than or equal to $20\ h^{-1}$, or even less than or equal to $10\ h^{-1}$. In embodiments, reforming unit 150 may operate at an LHSV greater than or equal to $0.1\ h^{-1}$ and less than or equal to $0.25\ h^{-1}$, greater than or equal to $0.25\ h^{-1}$ and less than or equal to $0.5\ h^{-1}$, greater than or equal to $0.5\ h^{-1}$ and less than or equal to $10\ h^{-1}$, greater than or equal to $10\ h^{-1}$ and less than or equal to $20\ h^{-1}$, greater than or equal to $20\ h^{-1}$ and less than or equal to $30\ h^{-1}$, or any and all sub-ranges formed from any of these endpoints.

In embodiments, the lean naphtha content of the reformate 313 may be greater than or equal to 40 wt. % and less than or equal to 95 wt. % In embodiments, the lean naphtha content of the reformate 313 may be greater than or equal to 50 wt. % and less than or equal to 85 wt. %. In embodiments, the lean naphtha content of the reformate 313 may be greater than or equal to 40 wt. %, greater than or equal to 45 wt. %, or even greater than or equal to 50 wt. %. In embodiments, the lean naphtha content of the reformate 313 may be less than or equal to 95 wt. %, less than or equal to 90 wt. %, or even less than or equal to 85 wt. %. In embodiments, the lean naphtha content of the reformate 313 may be greater than or equal to 40 wt. % and less than or equal to 45 wt. %, greater than or equal to 45 wt. % and less than or equal to 50 wt. %, greater than or equal to 50 wt. % and less than or equal to 85 wt. %, greater than or equal to 85 wt. % and less than or equal to 90 wt. %, greater than or equal to 90 wt. % and less than or equal to 95 wt. %, or any and all sub-ranges formed from any of these endpoints.

The reforming catalysts for catalytic reforming processes in the reforming unit 150 can be either mono-functional or bi-functional reforming catalysts, which can contain precious metals, such as one or more metals from Groups 8-10 of the IUPAC periodic table, as active components (Group VIIIB in the Chemical Abstracts Services (CAS) system). The metals may be supported on a catalyst support, such as but not limited to an alumina, silica, titania, or combination of these supports. The reforming catalyst can be a bi-functional catalyst that has both metal sites and acidic sites. The reforming catalyst may be a platinum or palladium supported on an alumina support. The composition of the unmixed isoparaffins stream 309, the impurities present in the unmixed isoparaffins stream 309, and the desired products in the reformate 313 may influence the selection of reforming catalyst, reforming process type, and operating conditions. Types of chemical reactions can be targeted by a selection of catalyst or operating conditions known to those of ordinary skill in the art to influence both the yield and selectivity of conversion of paraffinic and naphthenic hydrocarbon precursors to particular aromatic hydrocarbon structures.

In embodiments, the aromatics content of the reformate 313 may be greater than or equal to 30 wt. % and less than or equal to 95 wt. %. In embodiments, the aromatics content of the reformate 313 may be greater than or equal to 80 wt. % and less than or equal to 90 wt. %. In embodiments, the aromatics content of the reformate 313 may be greater than or equal to 30 wt. %, greater than or equal to 50 wt. %, or even greater than or equal to 70 wt. %. In embodiments, the aromatics content of the reformate 313 may be less than or equal to 95 wt. %, less than or equal to 92 wt. %, or even less than or equal to 90 wt. %. In embodiments, the aromatics content of the reformate 313 may be greater than or equal to 30 wt. % and less than or equal to 50 wt. %, greater than or equal to 50 wt. % and less than or equal to 70 wt. %, greater than or equal to 70 wt. % and less than or equal to 90 wt. %, greater than or equal to 90 wt. % and less than or equal to 92 wt. %, greater than or equal to 92 wt. % and less than or equal to 95 wt. %, or any and all sub-ranges formed from any of these endpoints.

BTX Separation Unit

In embodiments, the isoparaffin content of the mixed isoparaffins stream 315 may be greater than or equal to 10 wt. % and less than or equal to 50 wt. %. In embodiments, the isoparaffin content of the mixed isoparaffins stream 315 may be greater than or equal to 10 wt. %, greater than or equal to 15 wt. %, or even greater than or equal to 20 wt. %. In embodiments, the isoparaffin content of the mixed isoparaffins stream 315 may be less than or equal to 50 wt. %, less than or equal to 40 wt. %, or even less than or equal to 30 wt. %. The isoparaffin content of the mixed isoparaffins stream 315 may be greater than or equal to 10 wt. % and less than or equal to 15 wt. %, greater than or equal to 15 wt. % and less than or equal to 20 wt. %, greater than or equal to 20 wt. % and less than or equal to 30 wt. %, greater than or equal to 30 wt. % and less than or equal to 40 wt. %, greater than or equal to 40 wt. % and less than or equal to 50 wt. %, or any and all sub-ranges formed from any of these endpoints.

Still referring FIG. 3, the system 301 may include the BTX separation unit 300, which may be disposed downstream of the reforming unit 150. The BTX separation unit 300 may be in fluid communication with the isoparaffin aromatization catalytic unit 200 and may receive all or a portion of the mixed isoparaffins stream 315. The BTX separation unit 300 may include one or a plurality of separation units. The BTX separation unit 300 may be part of the separation system 30 as depicted in FIG. 1C.

The mixed isoparaffins stream 315 may be passed directly from the mixing of the liquid stream 323 and the reformate 313 to the BTX separation unit 300 without passing through any intervening reactor or separation system. The BTX separation unit 300 may be operable to separate the mixed isoparaffins stream 315 into at least the aromatics effluent 317 and the isoparaffins stream 319. The aromatics effluent 317 may comprise at least benzene, toluene, xylenes, and/or a combination of these. The isoparaffins stream 319 may comprise at least some isoparaffins. The BTX separation unit 300 may have any of the features or operating conditions previously described in the present disclosure for the BTX separation unit 300.

In embodiments, the isoparaffin content of the isoparaffins stream 319 may be greater than or equal to 30 wt. % and less than or equal to 70 wt. %. In embodiments, the isoparaffin content of the isoparaffins stream 319 may be greater than or equal to 30 wt. %, greater than or equal to 40 wt. %, or even greater than or equal to 50 wt. %. In embodiments, the isoparaffin content of the isoparaffins stream 319 may be less than or equal to 70 wt. % or even less than or equal to 60 wt. %. In embodiments, the isoparaffin content of the isoparaffins stream 319 may be greater than or equal to 30 wt. % and less than or equal to 40 wt. %, greater than or equal to 40 wt. % and less than or equal to 50 wt. %, greater than or equal to 50 wt. % and less than or equal to 60 wt. %, greater than or equal to 60 wt. % and less than or equal to 70 wt. %, or any and all sub-ranges formed from any of these endpoints.

In embodiments, the aromatics content of the aromatics effluent 317 may be greater than or equal to 60 wt. % and less than or equal to 95 wt. %. In embodiments, the aromatics content of the aromatics effluent 317 may be greater than or equal to 70 wt. % and less than or equal to 95 wt. %. In embodiments, the aromatics content of the aromatics effluent 317 may be greater than or equal to 60 wt. %, greater than or equal to 70 wt. %. In embodiments, the aromatics content of the aromatics effluent 317 may be less than or equal to 95 wt. % or even less than or equal to 85 wt. %. In embodiments, the aromatics content of the aromatics effluent 317 may be greater than or equal to 60 wt. % and less than or equal to 70 wt. %, greater than or equal to 70 wt. % and less than or equal to 85 wt. %, greater than or equal to 85 wt. % and less than or equal to 95 wt. %, or any and all sub-ranges formed from any of these endpoints.

Isoparaffin Aromatization Catalytic Unit

Still referring to FIG. 3, the system 301 may include the isoparaffin aromatization catalytic unit 200, which may be disposed downstream of the BTX separation unit 300. The isoparaffin aromatization catalytic unit 200 may be part of an aromatization system 20 that includes a gas/liquid separation unit 250 in addition to the isoparaffin aromatization catalytic unit 200 as depicted in FIG. 1B. The isoparaffin aromatization catalytic unit 200 may be in fluid communication with the BTX separation unit 300 and may receive all or a portion of the isoparaffins stream 319 BTX separation unit 300 from the BTX separation unit 300

Now referring again to FIG. 3, the isoparaffins stream 319 may be passed directly from the mixing of the liquid stream 323 and the unmixed isoparaffins stream 309 to the isoparaffin aromatization catalytic unit 200 without passing through any intervening reactor or separation system. The isoparaffin aromatization catalytic unit 200 may be operable to contact at least a portion of the isoparaffins stream 319 in the presence of at least one aromatization catalyst to produce an aromatization effluent 321. The isoparaffin aromatization catalytic unit 200 may have any of the features or operating conditions previously described in the present disclosure for the isoparaffin aromatization catalytic unit 200.

In embodiments, the aromatics content of the aromatization effluent 321 may be greater than or equal to 30 wt. % and less than or equal to 80 wt. %. In embodiments, the aromatics content of the aromatization effluent 321 may be greater than or equal to 30 wt. %, greater than or equal to 35 wt. %, greater than or equal to 40 wt. %, or even greater than or equal 45 wt. %. In embodiments, the aromatics content of the aromatization effluent 321 may be less than or equal to 80. %, less than or equal to 70 wt. %, or even less than or equal to 60 wt. %. In embodiments, the aromatics content of the aromatization effluent 321 may be greater than or equal to 30 wt. % and less than or equal to 35 wt. %, greater than or equal to 35 w. % and less than or equal to 40 wt. %, greater than or equal to 40 wt. % and less than or equal to 45 wt. %, greater than or equal to 45 wt. % and less than or equal to 60 wt. %, greater than or equal to 60 wt. % and less than or equal to 70 wt. %, or even greater than or equal to 70 wt. % and less than or equal to 80 wt. %, or any and all sub-ranges formed from any of these endpoints.

Gas/Liquid Separation Unit

Still referring to FIG. 3, the system 301 may include the gas/liquid separation unit 250, which may be disposed downstream of the isoparaffin aromatization catalytic unit 200. The gas/liquid separation unit 250 may be in fluid communication with the isoparaffin aromatization catalytic unit 200 and may receive all or a portion of the aromatization effluent 321 from the isoparaffin aromatization catalytic unit 200. The gas/liquid separation unit 250 may include one or a plurality of separation units.

The aromatization effluent 321 may be passed directly from the isoparaffin aromatization catalytic unit 200 to gas/liquid separation unit 250 without passing through any intervening reactor or separation system. The gas/liquid separation unit 250 may be operable to separate the aromatization effluent 321 into at least the gas stream 325 and the liquid stream 323. The gas/liquid separation unit 250 may have any of the features or operating conditions previously described in the present disclosure for the gas/liquid separation unit 250.

In embodiments, the aromatics content of the liquid stream 323 may be greater than or equal to 30 wt. % and less than or equal to 95 wt. %. In embodiments, the aromatics content of the liquid stream 323 may be greater than or equal to 70 wt. % and less than or equal to 95 wt. %. In embodiments, the aromatics content of the liquid stream 323 may be greater than or equal to 30 wt. %, greater than or equal to 35 wt. %, greater than or equal to 40 wt. %, or even greater than or equal 45 wt. %. In embodiments, the aromatics content of the liquid stream 323 may be less than or equal to 80. %, less than or equal to 70 wt. %, or even less than or equal to 60 wt. %. In embodiments, the aromatics content of the liquid stream 323 may be greater than or equal to 30 wt. % and less than or equal to 35 wt. %, greater than or equal to 35 w. % and less than or equal to 40 wt. %, greater than or equal to 40 wt. % and less than or equal to 45 wt. %, greater than or equal to 45 wt. % and less than or equal to 60 wt. %, greater than or equal to 60 wt. % and less than or equal to 70 wt. %, or even greater than or equal to 70 wt. % and less than or equal to 80 wt. %, or any and all sub-ranges formed from any of these endpoints.

In embodiments, the contents of the gas stream 325 in the system 301 may be alkanes and some light olefins separated from the aromatization effluent 321. The alkane composition of the gas stream 325 may be 1-25 wt. % methane, 1-25 wt. % ethane, 1-35 wt. % propane, and 1-35 wt. % butane. The light olefins content may be from 1-15 wt. %.

Steam Cracking Unit

Still referring to FIG. 3, the system 301 may include the steam cracking unit 500, which may be disposed downstream of the adsorption unit 100. The steam cracking unit 500 may be in fluid communication with the adsorption unit 100 and may receive all or a portion of the mixed paraffins stream 327.

In embodiments, the paraffin content of the mixed paraffins stream 327 may be greater than or equal to 15 wt. % and less than or equal to 45 wt. %. In embodiments, the paraffin content of the mixed paraffins stream 327 may be greater than or equal to 15 wt. %, greater than or equal to 20 wt. %, or even greater than or equal to 25 wt. %. In embodiments, the paraffin content of the mixed paraffins stream 327 may be less than or equal to 45 wt. %, less than or equal to 40 wt. %, or even less than or equal to 35 wt. %. In embodiments, the paraffin content of the mixed paraffins stream 327 may be greater than or equal to 15 wt. % and less than or equal to 20 wt. %, greater than or equal to 20 wt. % and less than or equal to 25 wt. %, greater than or equal to 25 wt. % and less than or equal to 35 wt. %, greater than or equal to 35 wt. % and less than or equal to 40 wt. %, greater than or equal to 40 wt. % and less than or equal to 45 wt. %, or any and all sub-ranges formed from any of these endpoints.

The mixed paraffins stream 327 may be passed directly from the low temperature stream 307 and the paraffins stream 311 to the steam cracking unit 500 without passing through any intervening reactor or separation system. The steam cracking unit 500 may be operable to crack at least a portion of the mixed paraffins stream 327 in the presence of at least one cracking catalyst to produce the ethylene stream 341. The steam cracking unit 500 may have any of the features or operating conditions previously described in the present disclosure for the steam cracking unit 500.

Gas Separation Unit

Still referring to FIG. 3, the system 301 may include the gas separation unit 400, which may be disposed downstream of the gas/liquid separation unit 250 and the steam cracking unit 500. The gas separation unit 400 may be in fluid communication with the gas/liquid separation unit 250 and the steam cracking unit 500. The gas separation unit 400 may receive all or a portion of the gas stream 325 from the gas/liquid separation unit 250 and all or a portion of the ethylene stream 341 from the steam cracking unit 500.

The gas stream 325 and the ethylene stream 341 may be passed directly from the gas/liquid separation unit 250 and the steam cracking unit 500 to the gas separation unit 400 without passing through any intervening reactor or separation system. The gas separation unit 400 may be operable to separate at least a portion of the gas stream 325 and the ethylene stream 341 into at least an olefins stream 343, a byproduct stream 345, and an aromatic-rich stream 347. The gas separation unit 400 may have any of the features or operating conditions previously described in the present disclosure for the gas separation unit 400.

EXAMPLES

The various embodiments of methods and systems for the processing of heavy oils will be further clarified by the following examples. The examples are illustrative in nature, and should not be understood to limit the subject matter of the present disclosure.

Example 1

In Example 1, the aromatization catalyst was synthesized. The zeolite preparation generally utilized the MFI organic template of tetrapropylammonium hydroxide (TPAOH, 1M). The specific molar ratio of the TPAOH template was mixed with RO (reverse osmosis) water, and then, a weight at least one of aluminum nitrate or aluminum sulfate octahydrate was added. The solution was mixed for 1-5 hours at room temperature with a mixing speed between 300-1000 rpm. A portion of tetraethyl orthosilicate (TEOS), silica gel, or fumed silica was added to the solution-contained template with aluminum salt. The solution was mixed for 2-10 hours at room temperature with a mixing speed between 300-1000 rpm.

The silica/alumina ratio of 50-150 was adjusted according to the solution molar ratio used for ZSM-5 preparation. In order to make a Si/Al ratio of 50, the molar ratio was adjusted to 1 $SiO_2$:0.02 $Al_2O_3$:58.57 $H_2O$:0.276 TPAOH. In order to make Si/Al ratio of 100, the molar ratio was adjusted to 1 $SiO_2$:0.01 $Al_2O_3$:58.57 $H_2O$:0.276 TPAOH. In order to make a Si/Al ratio of 150, the molar ratio was adjusted to 1 $SiO_2$:0.00665 $Al_2O_3$:58.57 $H_2O$:0.276 TPAOH.

Figure 4:
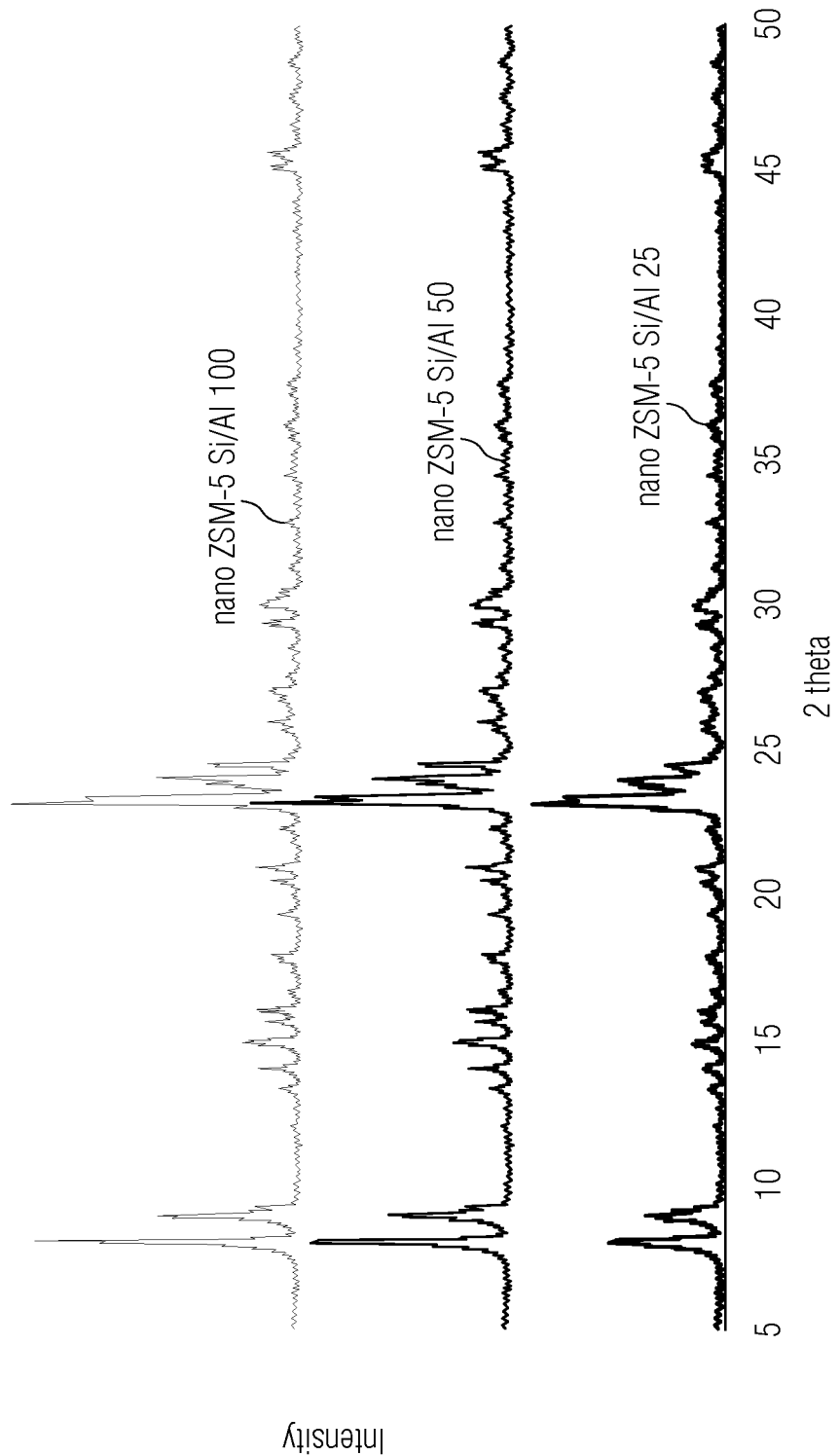
FIG. 4 graphically depicts X-ray diffraction spectra for an aromatization catalysts, according to one or more embodiments shown and described in the present disclosure.

Now referring to FIG. 4, the zeolite of varying Si/Al ratios is depicted using X-ray diffraction patterns. The aromatization catalysts having an Si/Al of 25, 50, and 100 showed the characteristic pattern of an MFI structure at $2\theta=7\text{-}10°$ and 20-24°, with crystallinity of 61.8%, 91.2%, and 100%, respectively.

The prepared solution of ZSM-5 zeolite was sent to a hydrothermal aging step at 170° C. for 15-24 hours in order to obtain a nanoscale crystal ZSM-5 between 100-750 nm. After the hydrothermally aging step, the ZSM-5 zeolite solution was sent to high speed counterfigure at speed of 10,000-50,000 rpm in order to recover ZSM-5 zeolite from solution. The ZSM-5 zeolite powder was then sent to the calcination oven, which is operated with static air or nitrogen gas. The temperature was set between 500-600° C. for 5-8 hours, in order to obtain zeolite after decomposition of organic template. The ZSM-5 zeolite was then treated with ammonium nitrate in order to form hydrogen of zeolite (H-ZSM-5) prepare for binding with an alumina binder between 20-60%. Modification of ZSM-5 was done by a thin layer with amorphous of silica, alumina, zinc oxide with silica or alumina, and/or phosphorus oxide with silica or alumina.

Figure 5A:
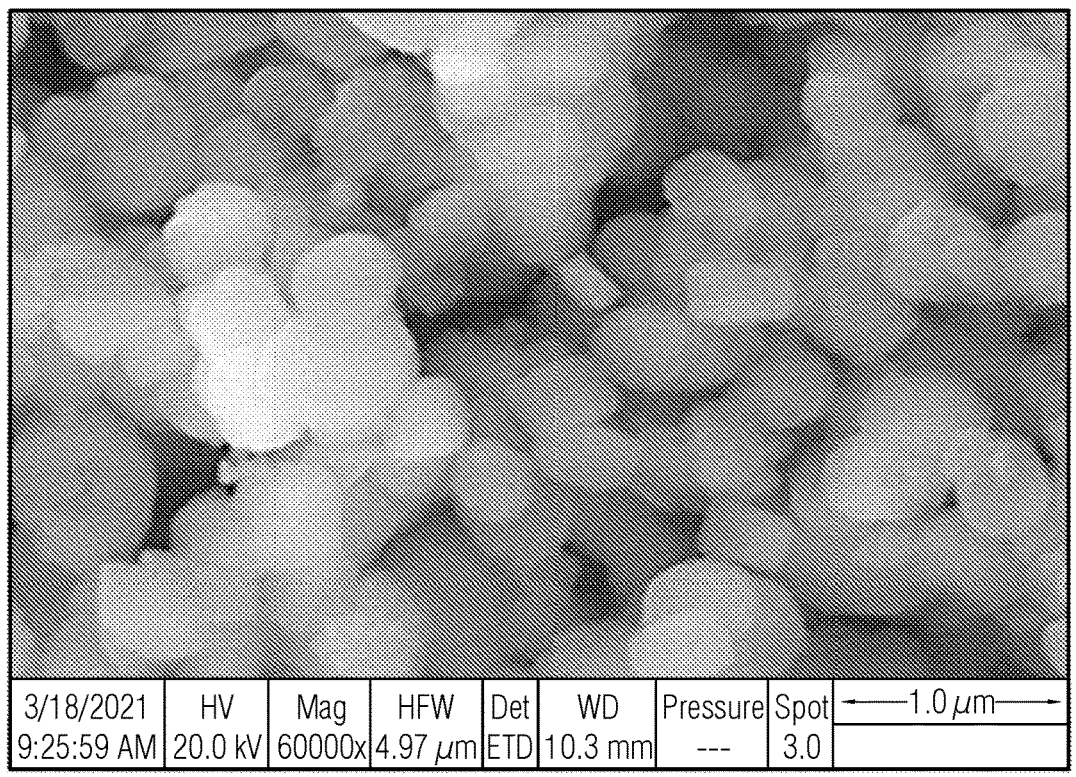
FIG. 5A depicts a photograph taken by a scanning electron microscope (SEM) of an aromatization catalyst, according to one or more embodiments shown and described in the present disclosure.
Figure 5B:
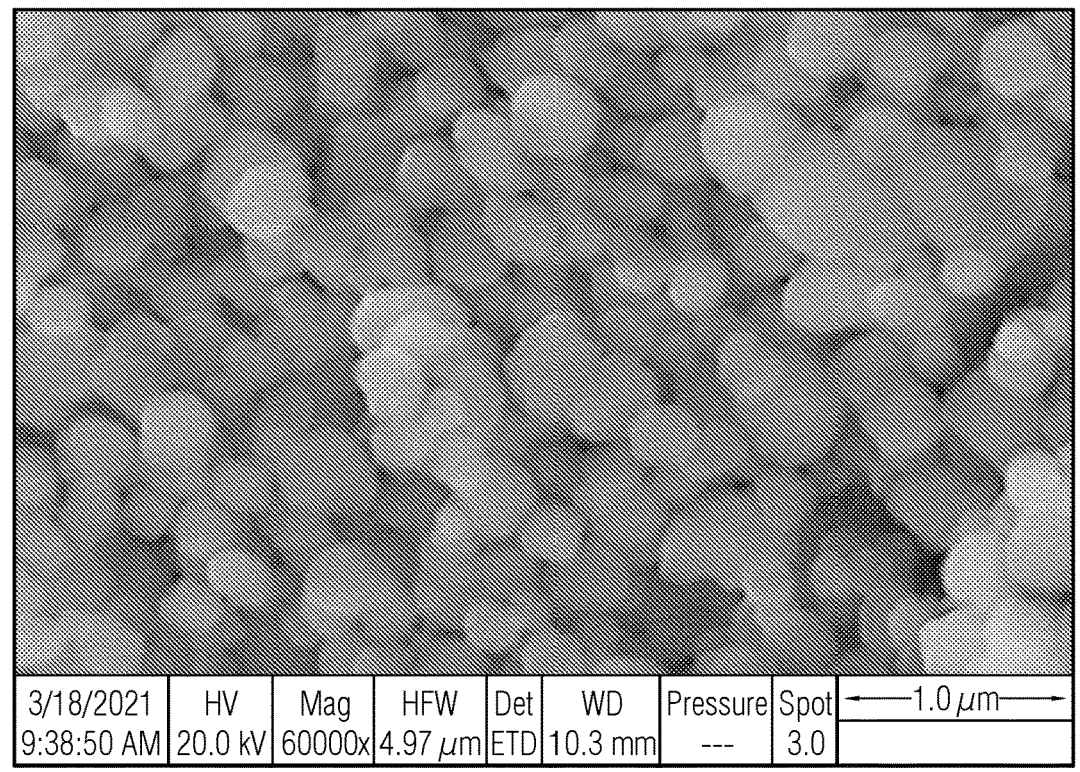
FIG. 5B depicts a photograph taken by a scanning electron microscope (SEM) of an aromatization catalyst, according to one or more embodiments shown and described in the present disclosure.

Now referring to FIGS. 5A and 5B, scanning electron microscope (SEM) images were obtained for the prepared aromatization catalyst. In FIG. 5A, the aromatization catalyst possesses well-ordered sharp-edges and square-looking crystallite morphology with a large crystal size of approximately 750 nm. The aromatization catalyst in FIG. 5B possesses a similar morphology. However, FIG. 5B was slightly deformed from square to spherical particles of sizes in the range of 200 nm to 450 nm.

Figure 6A:
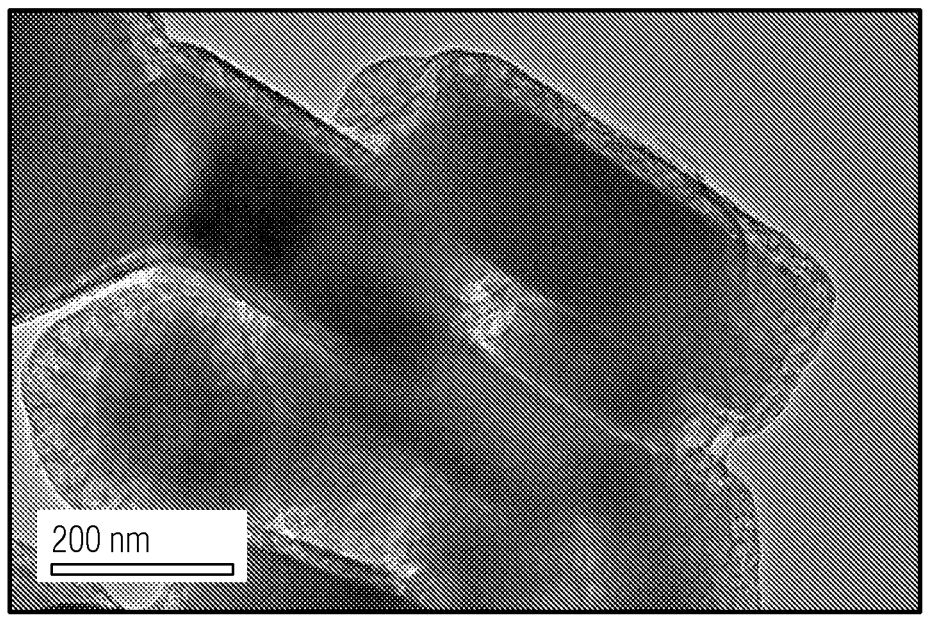
FIG. 6A depicts a photograph taken by a transmission electron microscope (TEM) of an aromatization catalyst, according to one or more embodiments shown and described in the present disclosure.
Figure 6B:
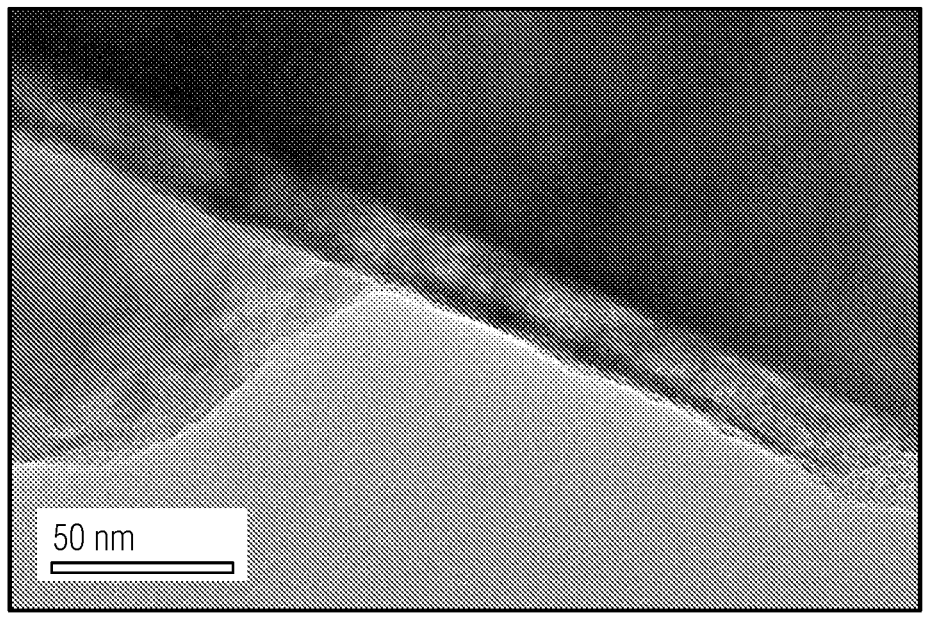
FIG. 6B depicts a photograph taken by a transmission electron microscope (TEM) of an aromatization catalyst, according to one or more embodiments shown and described in the present disclosure.

Now referring to FIGS. 6A and 6B, images from transmission electron microscopes (TEM) are depicted of nano ZSM-5 with a thin layer of amorphous silica. FIG. 6A depicts the thin layer of amorphous silica over the nano ZSM-5. FIG. 6B shows that the wall thickness of the thin layer of amorphous silica over the nano ZSM-5 is about 22 nm over nano ZSM-5.

Example 2

In Example 2, a feedstock comprising isomerate was sent to the isoparaffin aromatization catalytic fixed-bed reactor to convert the isoparaffin along with any paraffin content in the feedstock. The ZSM-5 MFI zeolite had a nano crystal size of 200-300 nm, and 20% binder was used. The fixed-bed aromatization reactor was heated to 450° C. without hydrogen. The reactor was pressurized to 10 bar using nitrogen gas before feedstock entered the reactor at space velocity of 1 $h^{-1}$. The hydrocarbon product was analyzed to determine the compositions (including BTX content) before and after aromatization. Table 1 shows the isoparaffin conversion achieved. BTX increased from 0.3 wt. % to 40 wt. %.

TABLE 1

| Product | Feed In | Product-Out |
| --- | --- | --- |
| Isoparaffin (wt. %) | 41.9 | 11.4 |
| Paraffin (wt. %) | 13.7 | 2.3 |
| Aromatics (wt. %) | 0.5 | 72.7 |
| Naphthenes (wt. %) | 43.9 | 13.6 |
| Olefin (wt. %) | 0 | 0 |
| BTX (wt. %) | 0.3 | 40 |
| Total sulfur (ppm) | <10 ppm | <10 ppm |

Example 3

In Example 3, a feedstock comprising whole naphtha was sent to the isoparaffin aromatization catalytic fixed-bed reactor to convert the isoparaffin along with paraffin fractions in the feedstock. The ZSM-5 MFI zeolite had a nano crystal size of 200-300 nm, and 20% binder was used. The fixed-bed reactor was heated to 450° C. without hydrogen. The reactor was pressurized to 10 bar using nitrogen gas before feedstock entered feedstock entered the reactor at space velocity of 1 $h^{-1}$. The hydrocarbon product was analyzed to determine the fractions and BTX content after and before conversion. Table 2 shows the isoparaffin conversion achieved. BTX increased from 12 wt. % to 49 wt. %.

TABLE 2

| Product | Feed In | Product-Out |
| --- | --- | --- |
| Isoparaffin (wt. %) | 32 | 11 |
| Paraffin (wt. %) | 33 | 9 |
| Aromatics (wt. %) | 16 | 69 |
| Naphthenes (wt. %) | 15 | 6 |
| Olefin (wt. %) | 4 | 5 |
| BTX (wt. %) | 12 | 49 |
| Total sulfur (ppm) | 292 | 168 |

Example 4

In Example 4, light naphtha was sent to the isoparaffin aromatization catalytic fixed-bed reactor to convert the isoparaffin content to aromatics. The ZSM-5 MFI zeolite had a nano crystal size of 500 nm, and the ZSM-5 was coated with 2% of silicon oxide in 40% binder. The fixed-bed reactor was heated to 450° C. without hydrogen. The reactor was pressurized to 10 bar using nitrogen gas before injecting the feedstock to the reactor at a space velocity of 1 hourly. The hydrocarbon product was analyzed to determine the fractions and BTX content before and after conversion. Table 3 shows the isoparaffin conversion achieved. BTX increased from 62.6 wt % to 84 wt. %.

TABLE 3

| Product | Feed In | Product-Out |
| --- | --- | --- |
| Isoparaffin (wt. %) | 10 | 5 |
| Paraffin (wt. %) | 24.5 | 10 |

TABLE 3-continued

| Product | Feed In | Product-Out |
| --- | --- | --- |
| Aromatics (wt. %) | 62.6 | 84 |
| Naphthenes (wt. %) | 1.9 | 0.7 |
| Olefin (wt. %) | 1 | 0.3 |
| BTX (wt. %) | 48 | 63.3 |
| Total sulfur (ppm) | 30 ppm | — |

Example 5

In Example 5, isomerate feedstock is sent to the isoparaffin aromatization catalytic fixed-bed reactor to convert the isoparaffin to aromatics. The ZSM-5 MFI zeolite had a nano crystal size of 200-300 nm, and the ZSM-5 was ion exchanged to coat zinc oxide (ZnO) over ZSM-5 MFI zeolite in 20% binder. The fixed-bed reactor operated at a higher temperature than the other Examples 2-4, at 600° C. without hydrogen. The reactor was pressurized to 10 bar using nitrogen gas before feedstock entered to the reactor at space velocity of 1 h$^{-1}$. The hydrocarbon product was analyzed to determine the fractions and BTX content before and after conversion. Table 4 shows the isoparaffin conversion was achieved. The BTX was increased BTX increased from 0.5 wt % to 95 wt. %.

TABLE 4

| Product | Feed In | Product-Out |
| --- | --- | --- |
| Isoparaffin (wt. %) | 41.9 | 0.4 |
| Paraffin (wt. %) | 13.7 | 0 |
| Aromatics (wt. %) | 0.5 | 95 |
| Naphthenes (wt. %) | 43.9 | 4.6 |
| Olefin (wt. %) | 0 | 0 |
| BTX (wt. %) | 0.3 | 46.7 |
| Total sulfur (ppm) | <10 ppm | <10 ppm |

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Any quantitative value expressed in the present application may be considered to include open-ended embodiments consistent with the transitional phrases "comprising" or "including."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

It is also noted that recitations herein of "at least one" component, element, etc., should not be used to create an inference that the alternative use of the articles "a" or "an" should be limited to a single component, element, etc.

Aspects

A first aspect of the disclosure is directed to a method for upgrading a naphtha feed, the method comprising: passing the naphtha feed to an adsorption unit to produce at least a paraffins stream and an isoparaffins stream, wherein the isoparaffin stream comprises isoparaffins and aromatics; and passing the isoparaffins stream to an isoparaffin aromatization catalytic unit that contacts the isoparaffins stream with at least one aromatization catalyst to produce aromatics from the isoparaffins thereby yielding an aromatization effluent, wherein the at least one aromatization catalyst comprises ZSM-5 zeolite.

In a second aspect of the present disclosure, in combination with the first aspect, further comprising separating out an aromatization effluent from the isoparaffins stream in a BTX separation unit, wherein the BTX separation unit is upstream of the isoparaffin aromatization catalytic unit, and wherein the aromatization effluent comprises benzene, toluene, and/or xylene (BTX).

In a third aspect of the present disclosure, in combination with the second aspect, wherein BTX is separated from the aromatization effluent by separating the aromatization effluent into a gas stream and a liquid stream in a gas/liquid separation unit, wherein the liquid stream contains benzene, toluene, and/or xylene; and passing the liquid stream back to the BTX separation unit.

In a fourth aspect of the present disclosure, in combination with any of the first through third aspects, further comprising passing the isoparaffins stream to a reforming unit to produce a reformate; and passing the reformate to a BTX separation unit.

In a fifth aspect of the present disclosure, in combination with any of the first through fourth aspects, wherein BTX is separated from the aromatization effluent by separating the aromatization effluent into a gas stream and a liquid stream in a gas/liquid separation unit, wherein the liquid stream contains benzene, toluene, and/or xylene; and passing the liquid stream to a BTX separation unit to produce an aromatics effluent and an unconverted aromatics stream, wherein the aromatics effluent contains benzene, toluene, and/or xylene.

In a sixth aspect of the present disclosure, in combination with the fifth aspect, further comprising passing the gas stream to a gas separation unit to produce an olefins stream, a byproduct stream, and an aromatic-rich stream.

In a seventh aspect of the present disclosure, in combination with the fifth aspect, further comprising passing the unconverted aromatics stream back to the adsorption unit.

In an eighth aspect of the present disclosure, in combination with the fifth aspect, further comprising passing the unconverted aromatics stream to a gasoline pool.

In a ninth aspect of the present disclosure, in combination with any of the first through eighth aspects, further comprising: passing the paraffin stream to a steam cracking unit to produce an ethylene stream; and passing the ethylene stream to a gas separation unit.

In a tenth aspect of the present disclosure, in combination with any of the first through ninth aspects, wherein the naphtha feed comprises from 30 weight percent (wt. %) to 60 wt. % isoparaffin based on a total weight of the naphtha feed.

In an eleventh aspect of the present disclosure, in combination with any of the first through tenth aspects, wherein the naphtha feed comprises from 20 wt. % to 40 wt. % isoparaffin based on a total weight of the naphtha feed and at least some aromatics.

In a twelfth aspect of the present disclosure, in combination with any of the first through eleventh aspects, further comprising: passing the naphtha feed to a splitter unit to produce a low temperature stream and a high temperature stream; and passing the high temperature stream to the adsorption unit.

In a thirteenth aspect of the present disclosure, in combination with any of the first through twelfth aspects, wherein conversion of isoparaffins in the isoparaffins stream to aromatics is from 40% to 80%.

In a fourteenth aspect of the present disclosure, in combination with any of the first through thirteenth aspects, wherein the isoparaffin aromatization catalytic unit operates at a temperature of from 300° C. to 600° C., a pressure of from 1 bar to 30 bar; and liquid hourly space velocity of from 0.2 $h^{-1}$ to 5 $h^{-1}$, wherein the isoparaffin aromatization catalytic unit comprises at least two fixed-bed, swing reactors.

In a fifteenth aspect of the present disclosure, in combination with any of the first through fourteenth aspects, wherein the ZSM-5 zeolite has a nano crystal scale between 100 nm and 750 nm.

In a sixteenth aspect of the present disclosure, in combination with any of the first through fifteenth aspects, wherein the paraffin stream comprises C1-C11 paraffins.

In a seventeenth aspect of the present disclosure, in combination with any of the first through sixteenth aspects, wherein the isoparaffin stream comprises from 0.1 ppm to 2000 ppm of sulfur.

What is claimed is:
1. A method for upgrading a naphtha feed, the method comprising:
    passing the naphtha feed to an adsorption unit to produce at least a paraffins stream and an isoparaffins stream, wherein the isoparaffin stream comprises isoparaffins and aromatics; and
    passing the isoparaffins stream to an isoparaffin aromatization catalytic unit that contacts the isoparaffins stream with at least one aromatization catalyst to produce aromatics from the isoparaffins thereby yielding an aromatization effluent, wherein the at least one aromatization catalyst comprises ZSM-5 zeolite.
2. The method of claim 1, further comprising separating out an aromatization effluent from the isoparaffins stream in a BTX separation unit, wherein the BTX separation unit is upstream of the isoparaffin aromatization catalytic unit, and wherein the aromatization effluent comprises benzene, toluene, and/or xylene (BTX).
3. The method of claim 2, wherein BTX is separated from the aromatization effluent by separating the aromatization effluent into a gas stream and a liquid stream in a gas/liquid separation unit, wherein the liquid stream contains benzene, toluene, and/or xylene; and passing the liquid stream back to the BTX separation unit.
4. The method of claim 1, further comprising passing the isoparaffins stream to a reforming unit to produce a reformate; and passing the reformate to a BTX separation unit.
5. The method of claim 1, wherein BTX is separated from the aromatization effluent by separating the aromatization effluent into a gas stream and a liquid stream in a gas/liquid separation unit, wherein the liquid stream contains benzene, toluene, and/or xylene; and
    passing the liquid stream to a BTX separation unit to produce an aromatics effluent and an unconverted aromatics stream, wherein the aromatics effluent contains benzene, toluene, and/or xylene.
6. The method of claim 5, further comprising passing the gas stream to a gas separation unit to produce an olefins stream, a byproduct stream, and an aromatic-rich stream.
7. The method of claim 5, further comprising passing the unconverted aromatics stream back to the adsorption unit.
8. The method of claim 5, further comprising passing the unconverted aromatics stream to a gasoline pool.
9. The method of claim 1, further comprising:
    passing the paraffin stream to a steam cracking unit to produce an ethylene stream; and
    passing the ethylene stream to a gas separation unit.
10. The method of claim 1, wherein the naphtha feed comprises from 30 weight percent (wt. %) to 60 wt. % isoparaffin based on a total weight of the naphtha feed.
11. The method of claim 1, wherein the naphtha feed comprises from 20 wt. % to 40 wt. % isoparaffin based on a total weight of the naphtha feed and at least some aromatics.
12. The method of claim 1, further comprising:
    passing the naphtha feed to a splitter unit to produce a low temperature stream and a high temperature stream; and
    passing the high temperature stream to the adsorption unit.
13. The method of claim 1, wherein conversion of isoparaffins in the isoparaffins stream to aromatics is from 40% to 80%.
14. The method of claim 1, wherein the isoparaffin aromatization catalytic unit operates at a temperature of from 300° C. to 600° C., a pressure of from 1 bar to 30 bar; and liquid hourly space velocity of from 0.2 $h^{-1}$ to 5 $h^{-1}$, wherein the isoparaffin aromatization catalytic unit comprises at least two fixed-bed, swing reactors.

15. The method of claim 1, wherein the ZSM-5 zeolite has a nano crystal scale between 100 nm and 750 nm.

16. The method of claim 1, wherein the paraffin stream comprises $C_1$-$C_{11}$ paraffins.

17. The method of claim 1, wherein the isoparaffin stream comprises from 0.1 ppm to 2000 ppm of sulfur.

\* \* \* \* \*